United States Patent [19]
Patterson et al.

[11] Patent Number: 5,902,263
[45] Date of Patent: May 11, 1999

[54] APPARATUS AND METHOD FOR REMOVING STENOTIC MATERIAL FROM STENTS

[75] Inventors: Greg R. Patterson, Pleasanton; G. Ronald Williams, Menlo Park; James J. Leary, Sunnyvale, all of Calif.

[73] Assignee: Prolifix Medical, Inc., Sunnyvale, Calif.

[21] Appl. No.: 08/998,333

[22] Filed: Dec. 24, 1997

Related U.S. Application Data

[62] Division of application No. 08/798,722, Feb. 12, 1997.

[51] Int. Cl.$^6$ .................................................. A61B 17/20
[52] U.S. Cl. ........................... 604/22; 606/159; 606/170
[58] Field of Search .......................... 604/22, 264, 280; 600/658, 571, 572; 606/159, 170

[56] References Cited

U.S. PATENT DOCUMENTS

| | | |
|---|---|---|
| 4,273,128 | 6/1981 | Lary . |
| 4,445,509 | 5/1984 | Auth . |
| 4,653,496 | 3/1987 | Bundy et al. . |
| 4,696,667 | 9/1987 | Masch . |
| 4,706,671 | 11/1987 | Weinrib . |
| 4,723,549 | 2/1988 | Wholey et al. . |
| 4,728,319 | 3/1988 | Masch . |
| 4,732,154 | 3/1988 | Shiber . |
| 4,790,812 | 12/1988 | Hawkins, Jr. et al. . |
| 4,792,130 | 12/1988 | Fogarty et al. . |

(List continued on next page.)

FOREIGN PATENT DOCUMENTS

| | | |
|---|---|---|
| 39 21 071 C2 | 2/1991 | Germany . |
| 9400027 | 1/1995 | Netherlands . |
| WO 95/29626 | 11/1995 | WIPO . |
| WO 97/17889 | 5/1997 | WIPO . |

OTHER PUBLICATIONS

Moris, M.D., Cesar et al. "Stenting for coronary dissection after balloon dilation of in–stent restenosis: Stenting a previously stented site," *Am Heart J*, 131:834–836 (1996).

Ghannem, M. et al. "Restenose Sur Endoprothese Coronaire: Traitement Par Implnation D'Une Nouvelle Endoprothese," *Ann, Cardiol. Angeol.*, 45(5):287–290 (1996).

Khanolkar, UB "Percutaneous Transluminal Rotational Atherectomy for Treatment of In–stent Restenosis," *Indian Heart J*, 48:281–282 (1996).

Schomig, M.D., Albert, et al. "Emergency Coronary Stenting for Dissection During Percutaneous Transluminal Coronary Angioplasty: Angiographic Follow–Up After Stenting and After Repeat Angioplasty of the Stented Segment," *JACC*, 23 (5):1053–1060 (1994).

Macander, M.D., Ph. D. Peter J., et al. "Balloon Angioplasty for Treatment of In–Stent Restenosis: Feasibility, Safety, and Efficacy," *Catheterization and Cardiovascular Diagnosis*, 32:125–131 (1994).

(List continued on next page.)

*Primary Examiner*—Wynn Wood Coggins
*Assistant Examiner*—Deborah Blyveis
*Attorney, Agent, or Firm*—Townsend and Townsend and Crew LLP

[57] ABSTRACT

Apparatus and methods are provided for recanalizing stented regions within the vasculature which have become restenosed. A shearing body is displaced within the stented region in order to dislodge the stenotic material from an interface envelope defined by the inner surface of the stent. Usually, the shearing body will be compliant and sized slightly larger than the stent in order to remove stenotic material substantially uniformly around the entire interface envelope. The shearing body may be in the form of a brush, helical row, spaced-apart disks, solid compressible body, or a variety of other specific configurations.

28 Claims, 12 Drawing Sheets

U.S. PATENT DOCUMENTS

| | | |
|---|---|---|
| 4,794,931 | 1/1989 | Yock . |
| 4,819,634 | 4/1989 | Shiber . |
| 4,842,579 | 6/1989 | Shiber . |
| 4,850,957 | 7/1989 | Summers . |
| 4,857,045 | 8/1989 | Rydell . |
| 4,857,046 | 8/1989 | Stevens et al. . |
| 4,867,156 | 9/1989 | Stack et al. . |
| 4,883,458 | 11/1989 | Shiber . |
| 4,886,061 | 12/1989 | Fischell et al. . |
| 4,890,611 | 1/1990 | Monfort et al. . |
| 4,894,051 | 1/1990 | Shiber . |
| 4,895,560 | 1/1990 | Papantonakos . |
| 4,926,858 | 5/1990 | Gifford, III et al. . |
| 4,966,604 | 10/1990 | Reiss . |
| 4,979,939 | 12/1990 | Shiber . |
| 4,979,951 | 12/1990 | Simpson . |
| 5,000,185 | 3/1991 | Yock . |
| 5,009,659 | 4/1991 | Hamlin et al. . |
| 5,011,488 | 4/1991 | Ginsburg . |
| 5,011,489 | 4/1991 | Salem . |
| 5,011,490 | 4/1991 | Fischell et al. . |
| 5,030,201 | 7/1991 | Palestrant ................................. 604/22 |
| 5,041,082 | 8/1991 | Shiber . |
| 5,047,040 | 9/1991 | Simpson et al. ........................ 606/159 |
| 5,071,424 | 12/1991 | Reger . |
| 5,078,723 | 1/1992 | Dance et al. . |
| 5,085,662 | 2/1992 | Willard . |
| 5,087,265 | 2/1992 | Summers . |
| 5,100,424 | 3/1992 | Jang et al. . |
| 5,116,352 | 5/1992 | Schnepp-Pesch et al. . |
| 5,135,483 | 8/1992 | Wagner et al. . |
| 5,154,724 | 10/1992 | Andrews . |
| 5,158,564 | 10/1992 | Schnepp-Pesch et al. . |
| 5,160,342 | 11/1992 | Reger et al. . |
| 5,176,693 | 1/1993 | Pannek, Jr. . |
| 5,192,291 | 3/1993 | Pannek, Jr. . |
| 5,195,954 | 3/1993 | Schnepp-Pesch et al. . |
| 5,196,024 | 3/1993 | Barath . |
| 5,209,749 | 5/1993 | Buelna . |
| 5,217,474 | 6/1993 | Zacca et al. . |
| 5,224,945 | 7/1993 | Pannek, Jr. . |
| 5,234,451 | 8/1993 | Osypka . |
| 5,269,751 | 12/1993 | Kaliman . |
| 5,308,354 | 5/1994 | Zacca et al. . |
| 5,314,438 | 5/1994 | Shturman . |
| 5,318,576 | 6/1994 | Plassche, Jr. et al. . |
| 5,320,634 | 6/1994 | Vigil et al. . |
| 5,334,211 | 8/1994 | Shiber . |
| 5,356,418 | 10/1994 | Shturman . |
| 5,360,432 | 11/1994 | Shturman . |
| 5,370,653 | 12/1994 | Cragg . |
| 5,376,100 | 12/1994 | Lefebvre . |
| 5,402,790 | 4/1995 | Jang et al. . |
| 5,423,799 | 6/1995 | Shiu ........................................ 606/159 |
| 5,427,115 | 6/1995 | Rowland et al. . |
| 5,443,443 | 8/1995 | Shiber . |
| 5,490,859 | 2/1996 | Mische et al. . |
| 5,527,326 | 6/1996 | Hermann et al. . |
| 5,535,756 | 7/1996 | Parasher . |
| 5,540,707 | 7/1996 | Ressemann et al. . |
| 5,554,163 | 9/1996 | Shturman . |
| 5,556,405 | 9/1996 | Lary . |
| 5,556,408 | 9/1996 | Farhat . |
| 5,578,018 | 11/1996 | Rowland et al. . |
| 5,643,297 | 7/1997 | Nordgren et al. . |
| 5,681,335 | 10/1997 | Serra et al. ............................. 606/159 |
| 5,702,413 | 12/1997 | Lafontaine |

OTHER PUBLICATIONS

Gordon, M.D., Paul C. "Mechanisms of Restenosis and Redilation Within Coronary Stents–Quantitative Angiographic Assessment," *JACC,* 21(5):1166–1174 1993).

Baim, M.D., Donald S. "Management of Restenosis Within the Palmaz–Schatz Coronary Stent (The U.S. Multicenter Experience)," *The American Journal of Caridiology,* 71:364–366 (1993).

Strauss, M.D., Bradley H., "Directional Atherectomy for Treatment of Restenosis Within Coronary Stents: Clinical, Angiographic and Histologic Results," *JACC,* 20(7):1465–1473 (1992).

Bowerman, M.D., Richard E., "Disruption of a Coronary Stent During Atherectomy for Restenosis," *Catheterization and Cardiovascular Diagnosis,* 24:248–251 (1991).

Haude, Michael et al. "Treatment of In–Stent Restenosis," Chapter 52, pp. 357–365.

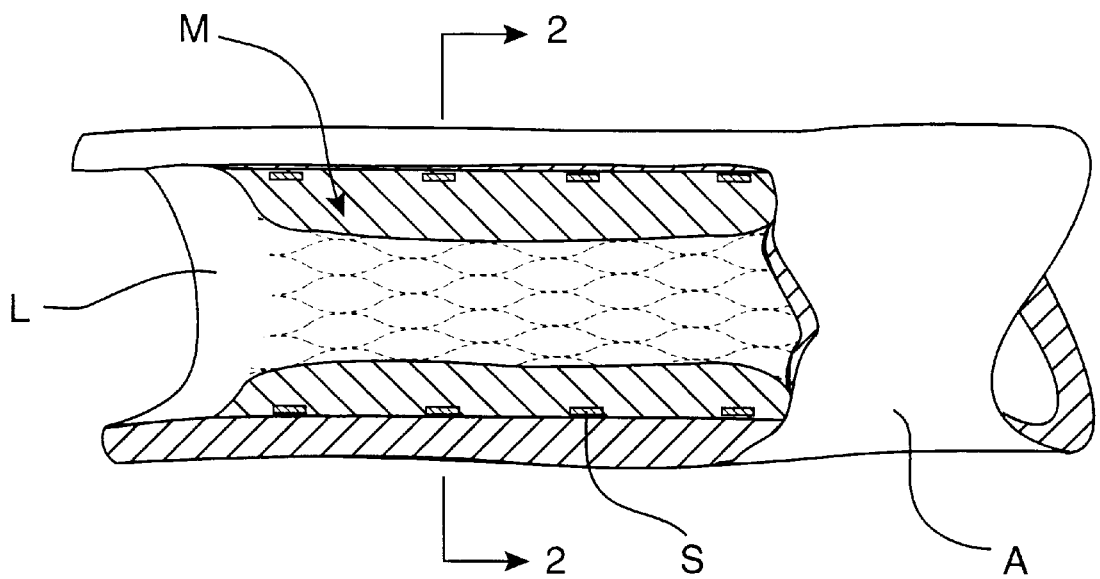
FIG_1
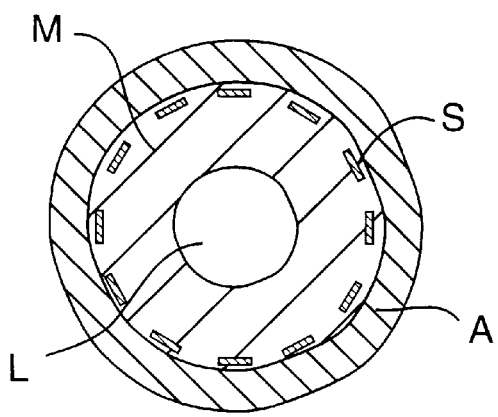
FIG_2

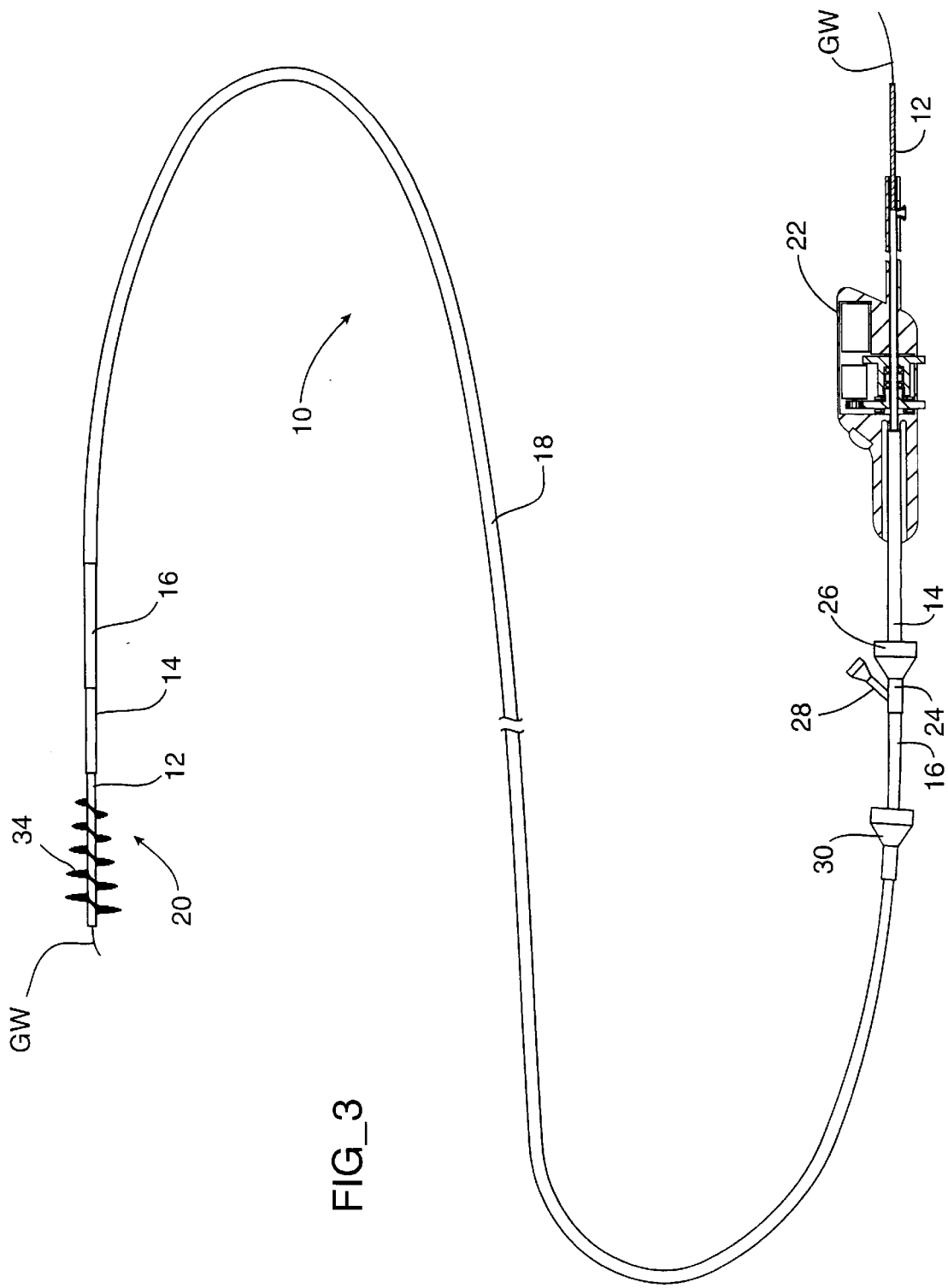
FIG_3

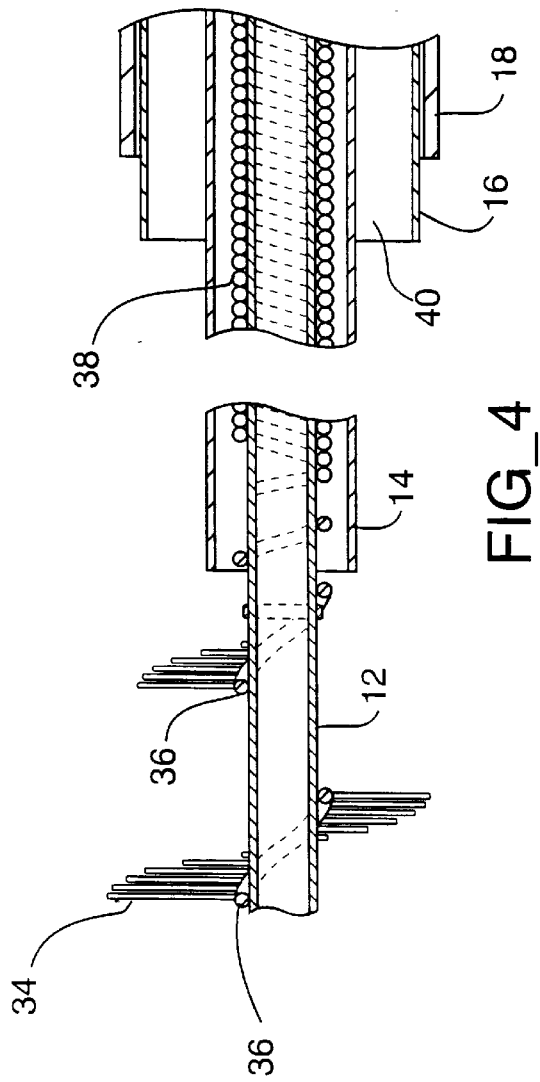
FIG_4
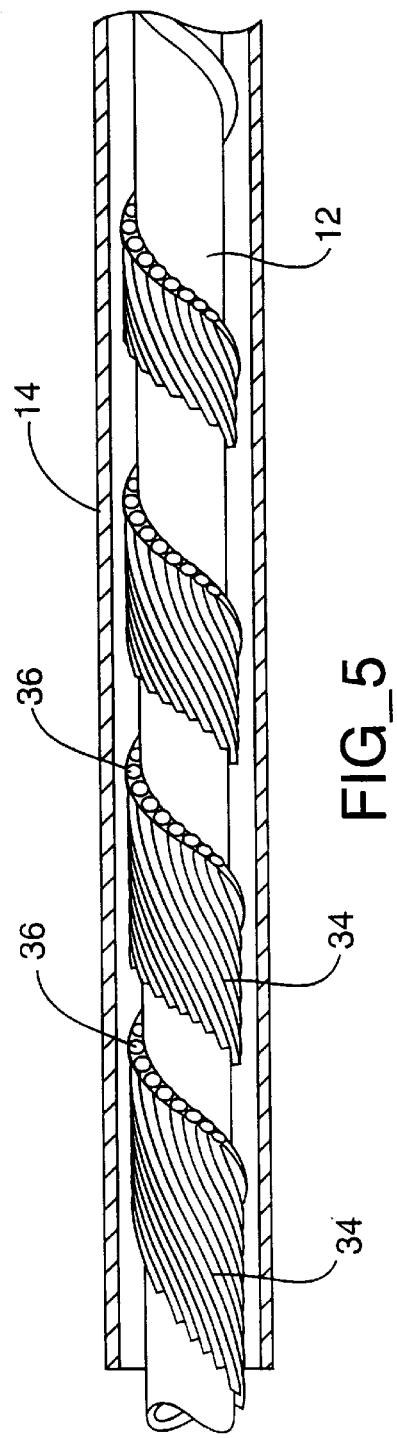
FIG_5

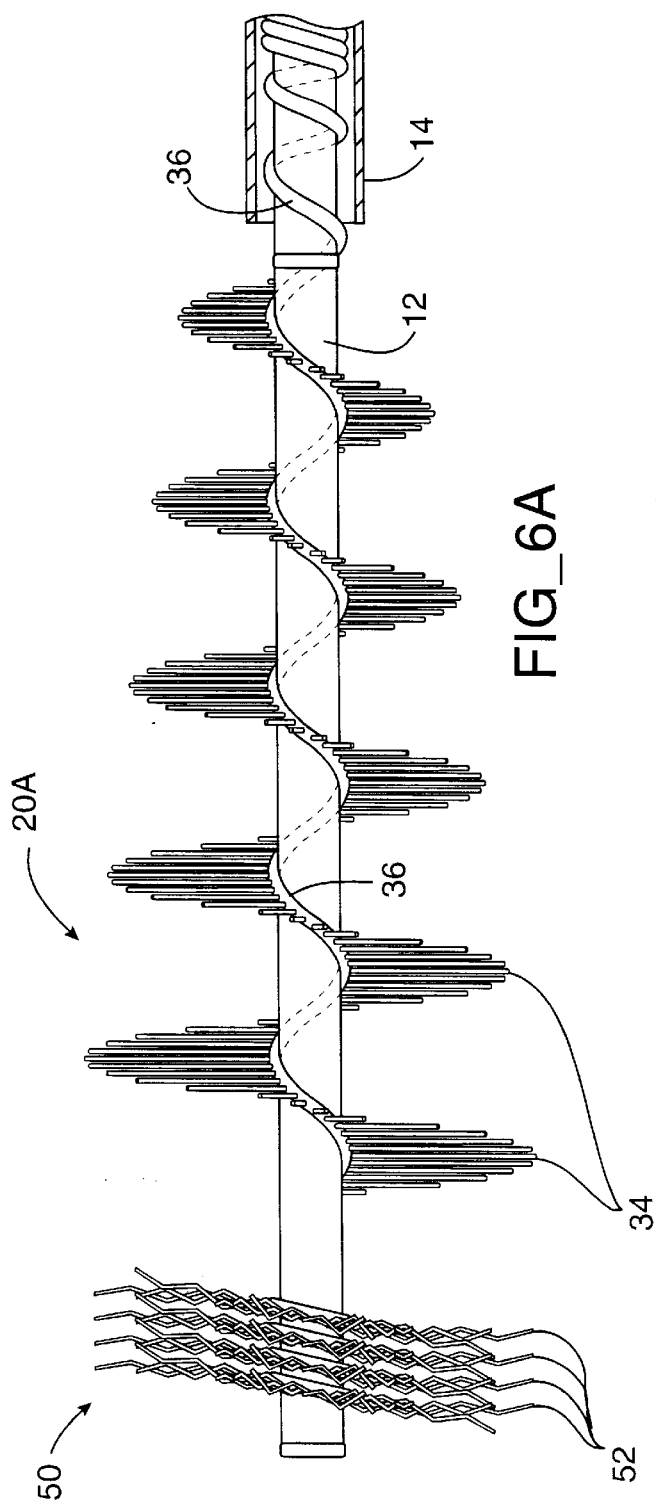
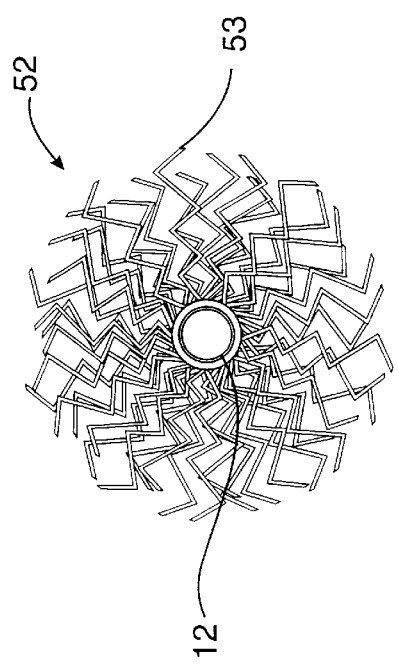

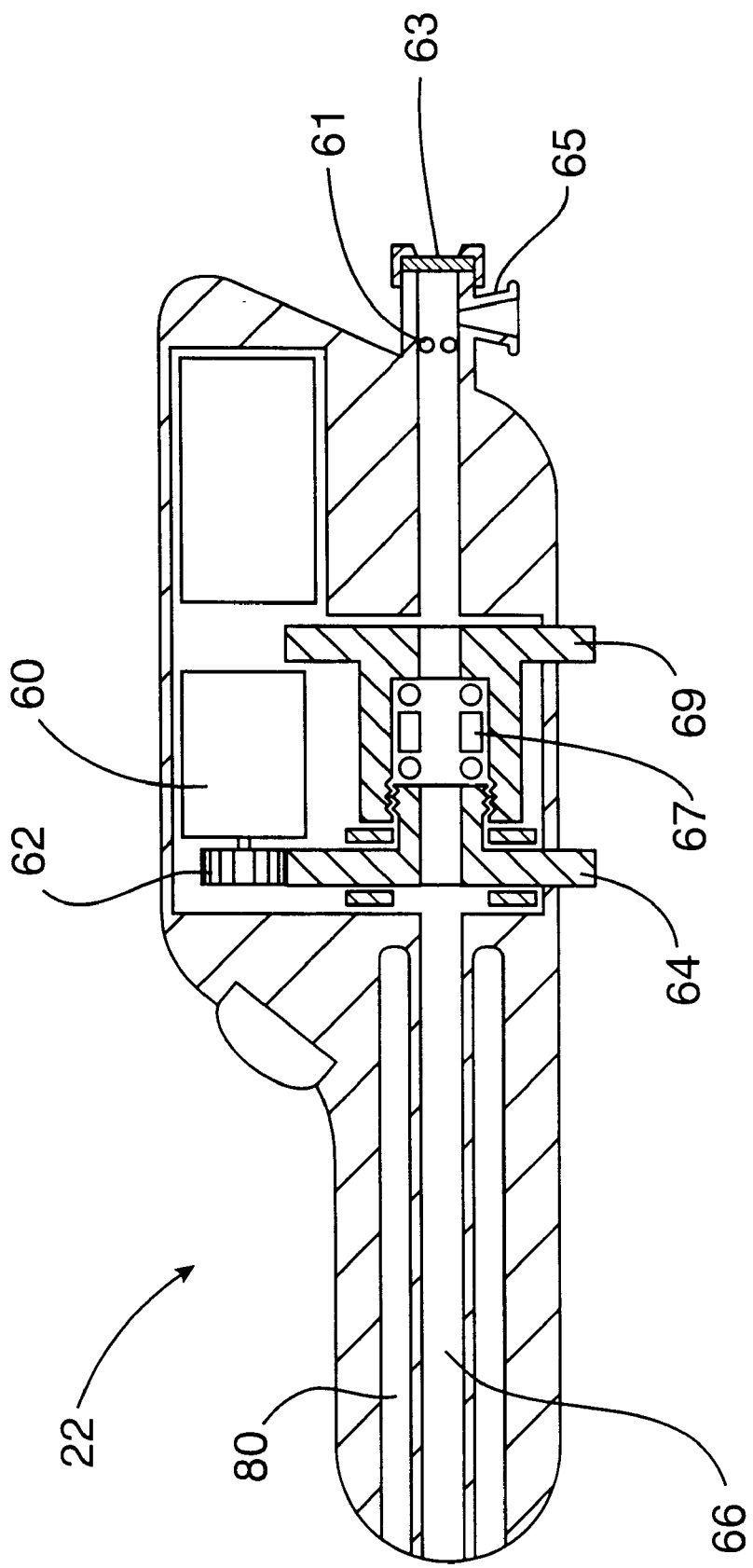
FIG_7

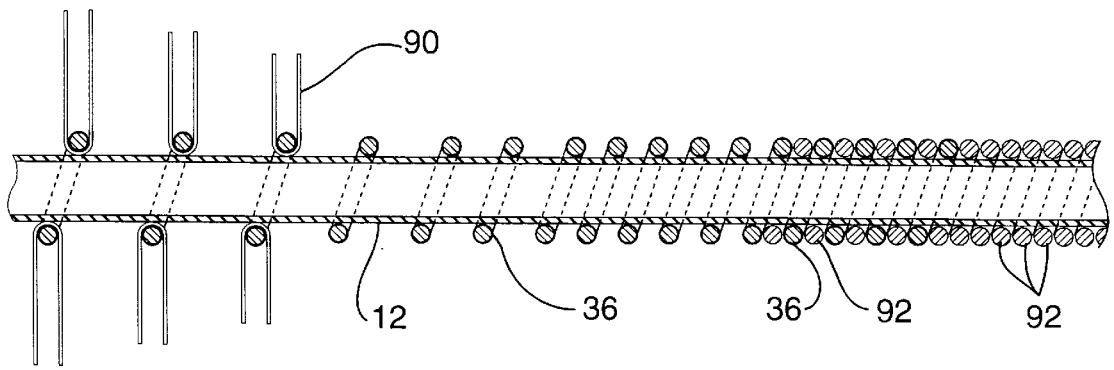
FIG_8
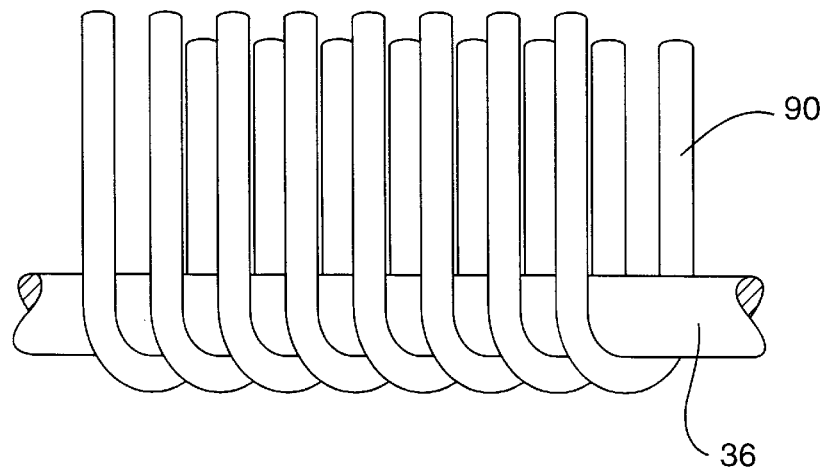
FIG_9

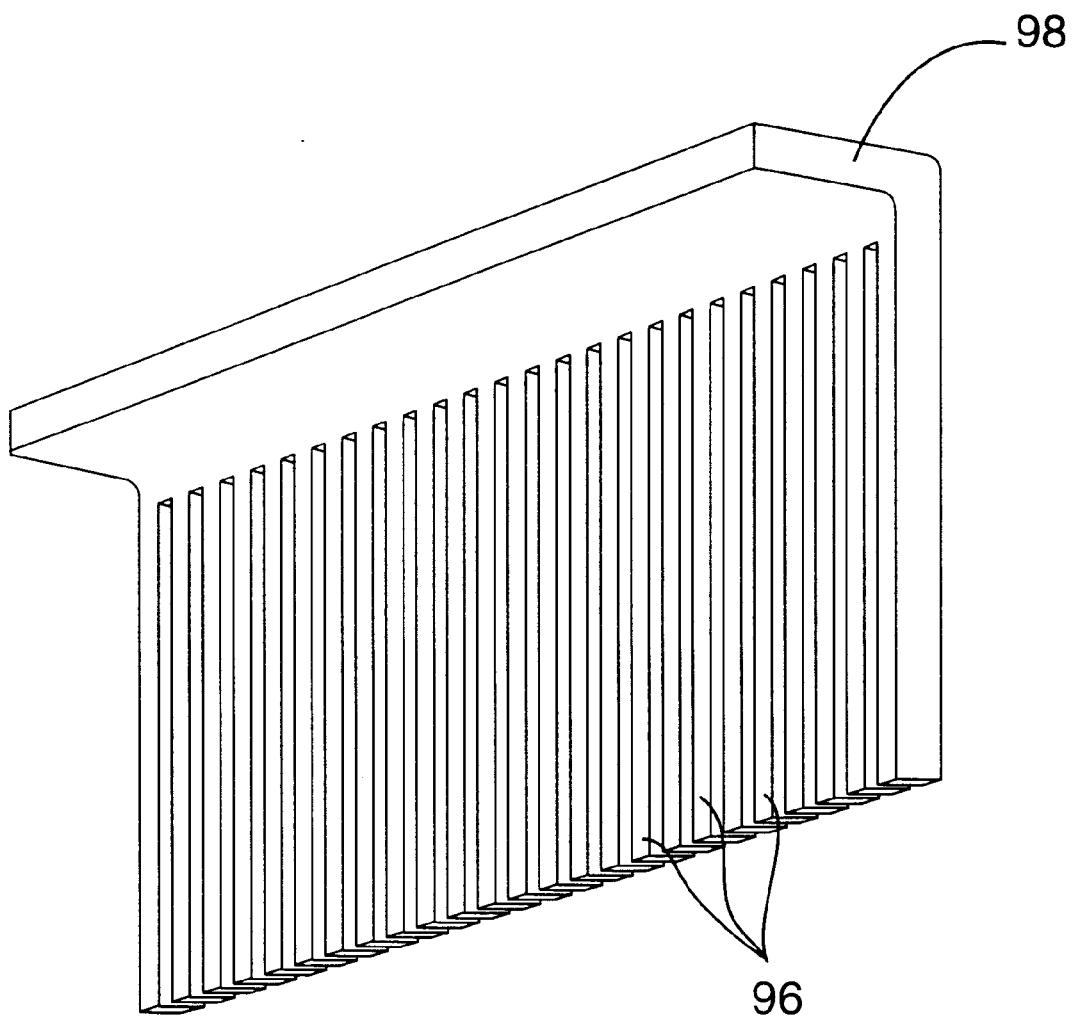
FIG_10

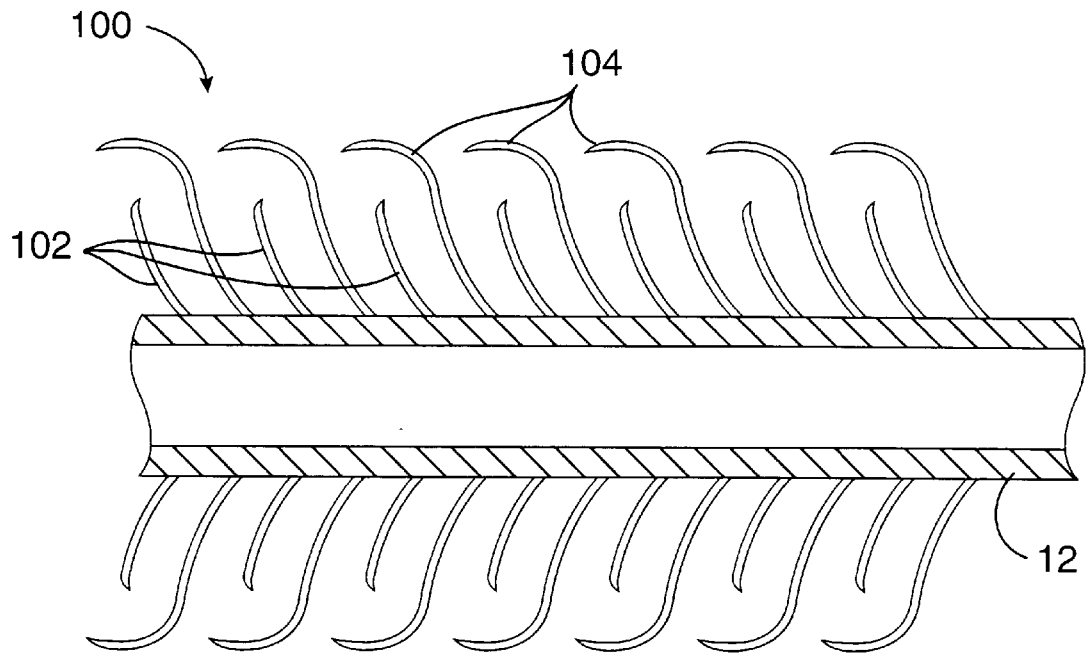
FIG_11
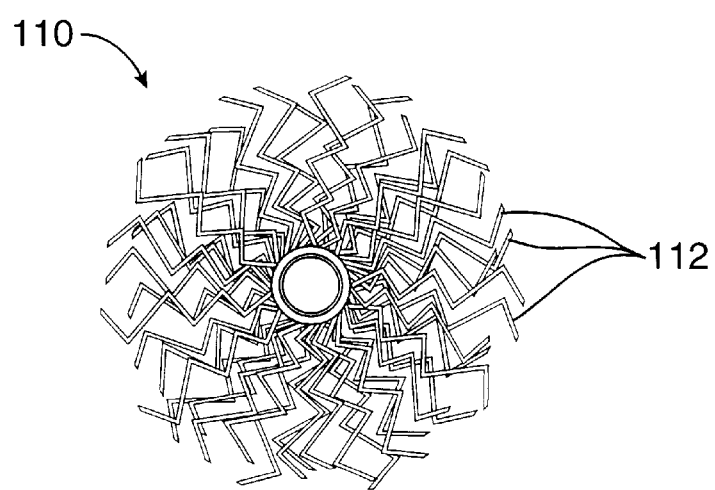
FIG_12

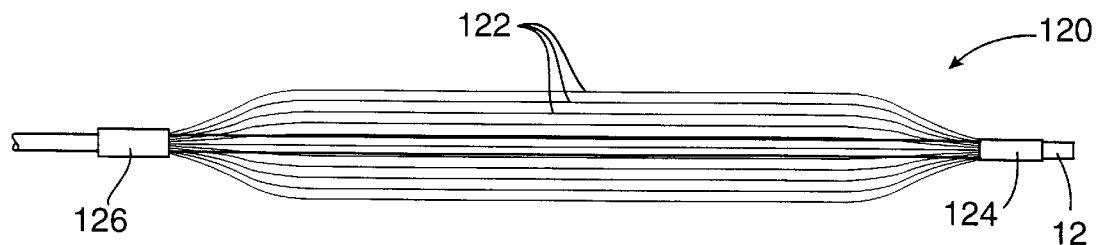
FIG_13
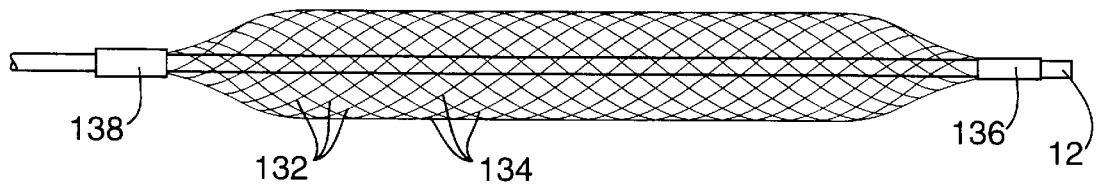
FIG_14
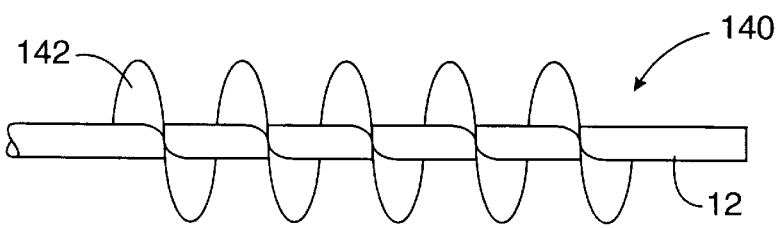
FIG_15
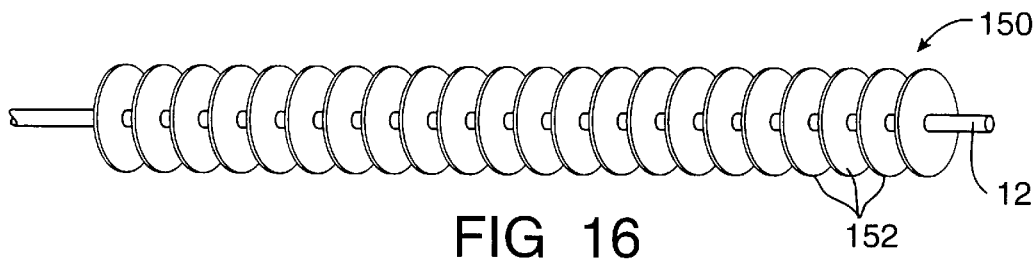
FIG_16
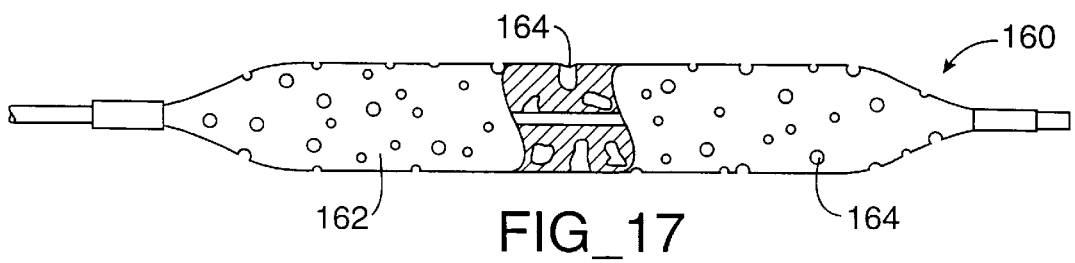
FIG_17

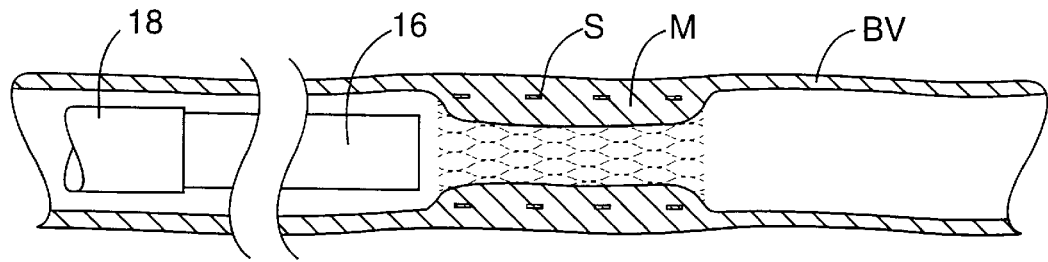
FIG_18A
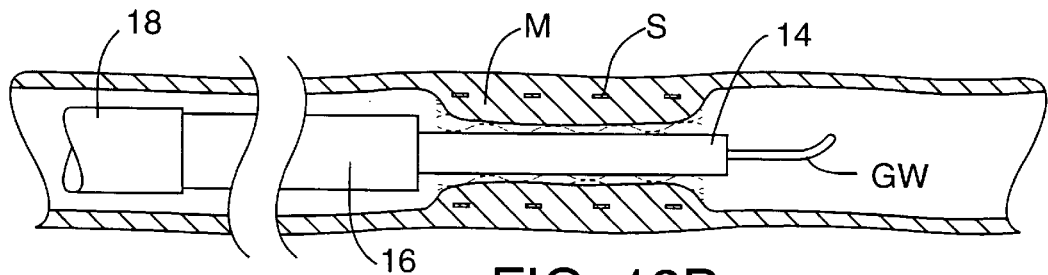
FIG_18B
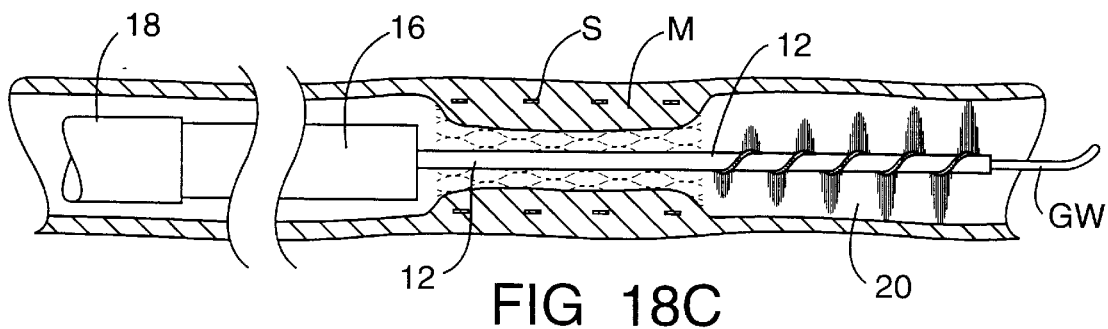
FIG_18C
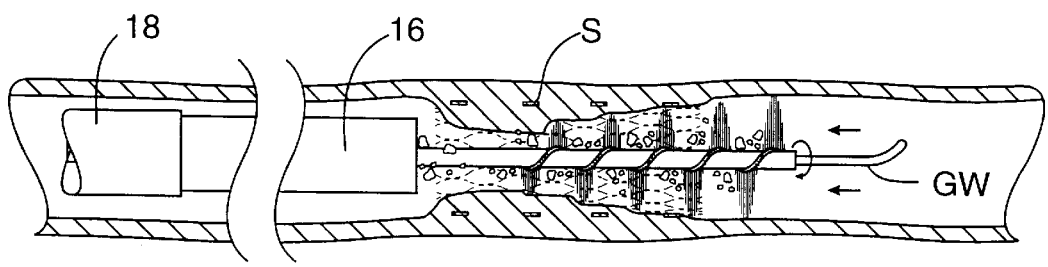
FIG_18D
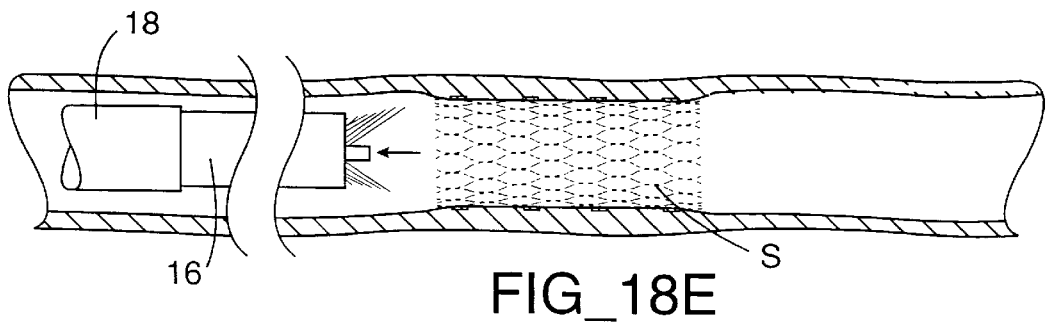
FIG_18E

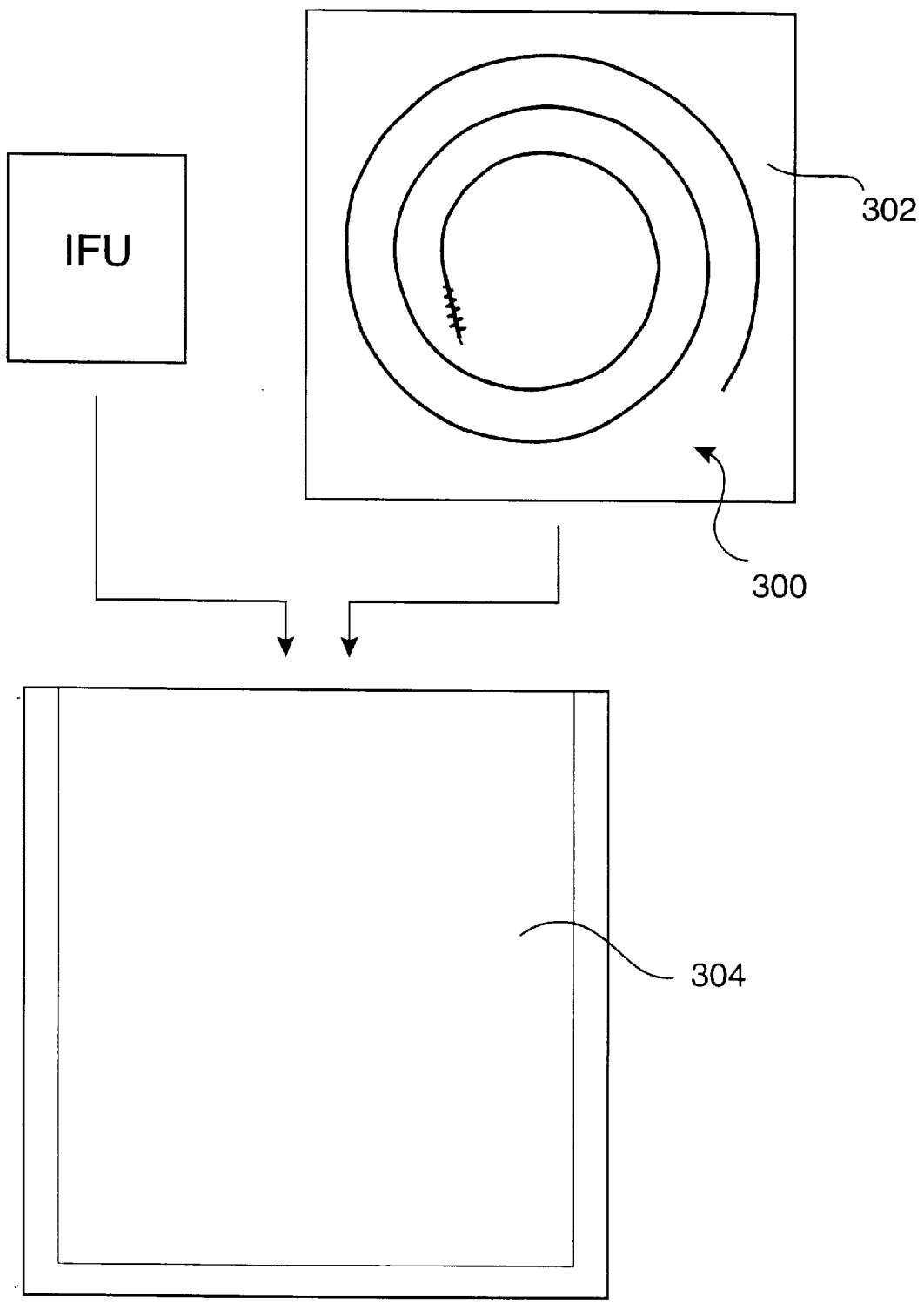
FIG_20

APPARATUS AND METHOD FOR REMOVING STENOTIC MATERIAL FROM STENTS

This is a division of U.S. application Ser. No. 08/798,722, filed Feb. 12, 1997, the full disclosure of which is incorporated by reference.

BACKGROUND OF THE INVENTION

1. Field of the Invention

The present invention relates generally to apparatus and methods for removing occluding material from stented regions within blood vessels which have restenosed. More particularly, the present invention relates to apparatus and methods for shearing the occluding material from around an interface envelope defined by the stent.

Percutaneous transluminal angioplasty (PTA) procedures are widely used for treating stenotic atherosclerotic regions of a patient's vasculature to restore adequate blood flow. Catheters having an expansible distal end, usually in the form of an inflatable balloon, are positioned in an artery, for example a coronary artery, at a stenotic site. The expansible end is then expanded to dilate the artery in order to restore adequate blood flow to regions beyond the stenosis. While PTA has gained wide acceptance, it suffers from two major problems: abrupt closure and restenosis.

Abrupt closure refers to rapid reocclusion of the vessel within hours of the initial treatment, and often occurs in patients who have recently suffered acute myocardial infarction. Abrupt closure often results from rapid thrombus formation which occurs in response to injury of the vascular wall from the initial PTA procedure. Restenosis refers to a re-narrowing of the artery over the weeks or months following an initial apparently successful PTA procedure. Restenosis occurs in up to 50% of all PTA patients and results at least in part from smooth muscle cell proliferation and migration.

Many different strategies have been proposed to ameliorate abrupt closure and reduce the restenosis rate. Of particular interest to the present invention, the implantation of vascular stents following PTA has become widespread. Stents are thin-walled tubular scaffolds which are expanded in the arterial lumen following the PTA procedure. Most commonly, the stents are formed from a malleable material, such as stainless steel, and are expanded in situ using a balloon. Alternatively, the stents may be formed from a shape memory alloy or other elastic material, in which case they are delivered in a radially constrained configuration and allowed to self-expand at the PTA treatment site. In either case, the stent acts as a mechanical support for the arterial wall, inhibiting both abrupt closure and restenosis.

While stents have been very successful in inhibiting abrupt closure and reasonably successful in inhibiting restenosis, a significant portion of the treated patient population still experiences restenosis over time. Most stent structures comprise an open lattice, typically in a diamond or a spiral pattern, and cell proliferation (often referred to as hyperplasia) can incur in the interstices between the support elements of the lattice. As a result, instead of forming a barrier to hyperplasia and restenosis, the stent can become embedded within an accumulated mass of thrombus and tissue growth, and the treatment site once again becomes occluded.

To date, proposed treatments for restenosis within previously stented regions of the coronary and other arteries have included both follow-up balloon angioplasty and directional atherectomy, e.g. using the Simpson atherectomy catheter available from Guidant Corporation, Sunnyvale, Calif. Neither approach has been wholly successful. Balloon angioplasty can temporarily open the arterial lumen, but rarely provides long-term patency. Directional atherectomy can successfully debulk the lumen within the stent, but rarely removes the material in a symmetric pattern. Moreover, it has been found that the atherectomy cutting blades can damage the stent, leaving protruding metallic pieces in the blood vessel lumen. Such discontinuities can act as sites for further thrombus formation.

For these reasons, it would be desirable to provide improved methods for treating restenosis within regions of the vasculature which have previously been implanted with stents. More particularly, it would be desirable to provide apparatus and methods for removing stenotic material from within the stents in a uniform and symmetric manner to provide a recanalized vascular lumen which is less likely to suffer from further restenosis. The apparatus and methods will preferably be capable of both dislodging the stenotic material and subsequently capturing and removing the dislodged material from the blood vessel lumen. Desirably, the apparatus will be able to dislodge and remove the stenotic material from along an interface envelope which is defined by the stent which has become embedded within the stenotic material. Removal will preferably be effected in a short amount of time, preferably using only a single or limited number of passes through the restenosed region within the stent. The apparatus and methods will be relatively easy to implement, present acceptable risks to the patient, and be readily performed by physicians who are familiar with balloon angioplasty and other conventional intravascular treatments. At least some of these objectives will be met by the various aspects of the present invention described below.

2. Description of the Background Art

Post-angioplasty restenosis is discussed in the following publications: Khanolkar (1996) *Indian Heart J.* 48:281–282; Ghannem et al. (1996) *Ann. Cardiol. Angeiol.* 45:287–290; Macander et al. (1994) *Cathet. Cardiovasc. Diagn.* 32:125–131; Strauss et al. (1992) *J. Am. Coll. Cardiol.* 20:1465–1473; Bowerman et al. (1991) *Cathet. Cardiovasc. Diagn.* 24:248–251; Moris et al. (1996) *Am. Heart. J.* 131:834–836; Schomig et al. (1994) *J. Am. Coll. Cardiol.* 23:1053–1060; Haude et al., "Treatment of In-Stent Restenosis," in *Endoluminal Stenting* 1996, Chapter 52, pages 357–365; Gordon et al. (1993) *J. Am. Coll. Cardiol.* 21:1166– 1174; and Baim et al. (1993) *Am. J. Cardiol.* 71:364–366. These publications include descriptions of follow-up angioplasty and atherectomy as possible treatments for restenosis.

Thrombectomy and atherectomy catheters having rotating brush and filament structures are described in U.S. Pat. Nos. 5,578,018; 5,535,756; 5,427,115; 5,370,653; 5,009,659; and 4,850,957; WO 95/29626; DE 39 21 071 C2; and Netherlands 9400027.

Representative atherectomy catheters are described in U.S. Pat. Nos. 4,273,128; 4,445,509; 4,653,496; 4,696,667; 4,706,671; 4,728,319; 4,732,154; 4,762,130; 4,790,812; 4,819,634; 4,842,579; 4,857,045; 4,857,046; 4,867,156; 4,883,458; 4,886,061; 4,890,611; 4,894,051; 4,895,560; 4,926,858; 4,966,604; 4,979,939; 4,979,951; 5,011,488; 5,011,489; 5,011,490; 5,041,082; 5,047,040; 5,071,424; 5,078,723; 5,085,662; 5,087,265; 5,116,352; 5,135,483; 5,154,724; 5,158,564; 5,160,342; 5,176,693; 5,192,291; 5,195,954; 5,196,024; 5,209,749; 5,217,474; 5,224,945; 5,234,451; 5,269,751; 5,308,354; 5,314,438; 5,318,576;

5,320,634; 5,334,211; 5,356,418; 5,360,432; 5,376,100; 5,402,790; 5,443,443; 5,490,859; 5,527,326; 5,540,707; 5,556,405; 5,556,408; and 5,554,163.

SUMMARY OF THE INVENTION

The present invention provides apparatus and methods for removing stenotic material from within previously stented regions of a patient's vasculature. The present invention is particularly intended for treating regions of restenosis within the stent which result from the accumulation of cellular, thrombotic, and other material over the weeks and months following an initially successful stent placement. The present invention will also be useful for treating relatively rapid thrombus formation which may sometimes occur during the hours and days immediately following a stent placement procedure.

Methods according to the present invention comprise displacing a shearing body within a stented region within a blood vessel, usually a coronary or other artery, which has become restenosed or otherwise occluded following the initial stent placement. The shearing body may be axially translated and/or rotated within the stented region, usually being rotated while it is simultaneously translated in order to effect a uniform shearing action over an interface envelope defined by the stent within an accumulation of occluding material. The shearing body will preferably have a width which is sufficient to engage substantially the entire periphery of the stent interface envelope as the shearing body is displaced therein. Usually, the shearing body will be compliant and slightly over-sized so that it engages and sweeps the entire interface envelope as it is displaced therein. Alternatively, or additionally, the width of the shearing body may be selectively adjusted so that it conforms to the size of the stent interface, again typically being adjusted so that it is slightly oversized and compliant against the interface envelope. Thus, the present invention relies at least in part on the stent itself to define the region which is to be recanalized within the blood vessel.

The methods of the present invention will optionally further comprise collecting and removing the dislodged stenotic material from the blood vessel. Collection and removal will most often be accomplished using the same catheter or catheter assembly which carries the shearing body, typically by aspiration, entrapment, filtering, or some combination thereof. It will be appreciated that various catheter assemblies can be put together using coaxially arranged components which may be introduced through a single vascular access site, typically a femoral access tract. Alternatively, collection and removal may be accomplished using separate collection apparatus, such as a catheter or catheter assembly, which is introduced through a separate access point. The separate catheter or catheter assembly would rely on similar collection capabilities, such as aspiration, filtering, entrapment, or the like, and will typically be located on the side of the stenosed region opposite to that from which the shearing body is accessed. In some instances, it may be desirable to partially or totally isolate the stented region from circulation during recanalization. For example, embolic filters may be placed upstream and downstream of the stented region. Alternatively, spaced-apart balloons may be used to fully isolate the isolated region, although such isolation should not be performed for an extended time period which can result in ischemia.

As stated above, the shearing body is preferably compliant and will have a width (diameter in the case of circular cross-sections) which is at least slightly greater than the interior width or diameter of the interface envelope created by the stent. Typically, the shearing body will be selected to have a width which is from 1% to 25% greater than that of the interior width or diameter of the interface envelope, preferably being from 2% to 20% greater, and more preferably being from 5% to 15% greater. Most often, the shearing body will have a generally round cross-section, and the width will be equal to the diameter. The cross-section, however, need not be circular, and in some instances it may be desirable to provide a polygonal cross-section, an irregular cross-section, a cross-section having surface texture such as ribs or protrusions, or the like.

The shearing body will have an exterior surface or region capable of dislodging stenotic material at the stent interface envelope as the shearing body is displaced therein. In particular, the exterior surface will include features, elements, texturing, or the like which will shear and/or abrade the stenotic material over the interface envelope defined by the interior of the stent as the shearing body is displaced therein.

For example, the shearing body may be a brush having a plurality of radially disposed filaments, where the distal tip of each filament can act to abrade stenotic material from within the stent interface envelope as the brush is rotated and/or axially translated. In a preferred aspect of the present invention, the brush comprises a helical row of filaments, usually being tapered with a small diameter at the end which first enters the stented region to be treated. Alternatively, a brush structure could comprise a series of spaced-apart disk, axially aligned rows, or other non-continuous structures. The use of brushes having relatively large openings between filament structures is advantageous and permits the stenotic material to be accumulated with these voids. Thus, the material may be trapped within the shearing body itself as the shearing body is contained and removed from the blood vessel. The filaments can be composed of polymeric materials, e.g. polyethylenes, polyethyleneterephthalates, polypropylenes, polyimides, polyamides (nylons), and copolymers thereof, or can be composed of metals, e.g. stainless steel, nickel-titanium alloys (nitinols), titanium alloys, cobalt alloys, and the like. The brushes may be formed from filaments of a single material or may be formed from individual filaments composed of two or more different materials. The individual filaments themselves may be formed from more than one material, e.g. polymeric coated metal wires, or the like.

A variety of other particular structures for the shearing body are also possible. For example, the shearing body may comprise one or more continuous webs of materials (e.g. fabrics, membranes, or the like) which are arranged to project radially outward to define the shearing body. The webs may be formed from natural or synthetic materials or fibers, usually being synthetic polymers, such as polyethylenes, polyethyleneterephthalates, polypropylenes, polyimides, polyamides (nylons), polyurethanes, latex, silicone, rubber, and copolymers and mixtures thereof. Fabrics may be formed by weaving different fibers together, and may optionally be reinforced using metal fibers or filaments, where the metals may be any of the materials described above for use as brush filaments. Such continuous webs may be arranged as a continuous helical row, as a series of spaced-apart disks, or in a variety of other specific configurations. In many ways, the use of continuous webs of material will be analogous to the use of brush filaments arranged in helical or disk-like patterns. Rotation and translation of such shearing bodies will act both to dislodge the stenotic material and entrap the dislodged material within voids present between successive turns or disks of the web.

As yet another alternative, the shearing body may comprise a cage or similar lattice structure comprising individual elements which act to shear the stenotic material as the shearing body is rotated and/or axially translated through the stented region being treated. Usually, but not necessarily, the cage structures will be selectively expandable so that the user can adjust the width or diameter in situ. Most often, the axial length of the cage structure will be adjustable so that the radius can be increased and/or decreased. The cage structure will usually be compliant so that it will be slightly compressed against the interface envelope of the stent as it is displaced therein. An advantage of the use of such cage structures is that the removed stenotic material may be at least partially entrapped within the cage, facilitating removal of the material from the vasculature. The cage structures may be fabricated from a variety of materials, including both metals and polymers, and the materials may be selected so that they are softer than the stent to reduce the likelihood that the stent will be damaged during the removal process.

In a preferred aspect of the method of the present invention, a catheter is positioned on one side of the stented region. The shearing body is positioned on the opposite side of the stent and then translated through the stented region toward the distal end of the catheter to dislodge stenotic material from the interface envelope defined by the stent. The dislodged stenotic material is typically aspirated or otherwise collected into the distal end of the catheter. Usually, but not necessarily, the shearing body will be deployed from the same catheter or catheter assembly which is used to aspirate or otherwise collect the dislodged stenotic material. For example, the catheter may first be positioned on one side of the stented region, the shearing body passed though the stented region in a collapsed or non-deployed configuration, and the shearing body then deployed on the opposite side of the stented region from the catheter. The deployed shearing body may then be drawn proximally back toward the catheter or catheter assembly with the dislodged material being aspirated into such catheter or catheter assembly. Deployment may comprise releasing the shearing body from radial constraint. Alternatively, deployment may comprise actively and selectively increasing the diameter of the shearing body, such as a cage structure, by the techniques described above. Also as described above, separately introduced catheters or catheter assemblies may be used for aspiration/collection and for shearing body deployment.

In yet another aspect of the present invention, the method is characterized by use of a shearing body having a cross-sectional geometry which is sufficiently large to engage in the entire interior surface of the stent when the shearing body is displaced therein. Use of such a shearing body results in substantially uniform displacement and dislodgement of the stenotic material from the interface envelope defined by the stent.

In yet another particular aspect of the present invention, the method is characterized by rotation and translation of the compliant shearing body through the stented region, wherein at least a portion of the compliant shearing body has a width which is greater than the diameter of the stent so that the shearing body is compressed by the stent as it passes therethrough.

In still yet another specific aspect of the present invention, the method is characterized by rotating and translating a tapered shearing body through the stented region, where a small width end of the tapered shearing body enters the stented region first.

In a still further specific aspect of the present invention, the method is characterized by rotation and translation of a brush assembly through the stenosed stented region being treated.

In one more specific aspect of the present invention, the method is characterized by rotation and translation of a helical shearing body through the stented region.

Apparatus according to the present invention include catheters, catheter systems, and catheter kits which are specially intended and adapted for performing the methods described above. In particular, the apparatus are designed to afford percutaneous intravascular placement of the shearing body at the site of restenosis within a previously stented region of the vasculature. To that end, catheter systems according to the present invention may comprise an inner catheter shaft having a proximal end and a distal end. The shearing body, usually being radially compressible, is disposed near the distal end of the catheter shaft, and a sheath is slidably coupled to the inner catheter. The sheath has a cavity near its distal end, where the cavity receives the shearing body to effect radial constraint and containment. The shearing body may have any of the structures described above. The catheter system will usually further include an outer catheter tube having a proximal end, a distal end, and a inner lumen. The outer catheter tube will usually have an aspiration port near its proximal end so that dislodged stenotic material can be aspirated from the vasculature. This catheter system is particularly suited for introducing the shearing body in its radially collapsed configuration through the stented region to a side of the stented region opposite to the location of the catheter. The shearing body is then released from the sheath, and the deployed shearing body drawn back toward the catheter to dislodge the stenotic material as generally described above. The dislodged material may then be aspirated through the outer catheter tube.

Preferably, the inner catheter shaft of the catheter system will have a guidewire lumen extending therethrough. The guidewire lumen is useful for positioning the catheter system over a guidewire in a conventional manner. The inner catheter shaft usually has a diameter in the range from about 0.2 mm to 1 mm, more usually from 0.3 mm to 0.6 mm. The shearing body has a maximum width when radially unconstrained in the range from 2 mm to 5 mm, preferably from 3 mm to 4 mm. The sheath cavity has a diameter in the range from 0.5 mm to 2 mm, usually from 0.75 mm to 1 mm, and the outer tube has a lumen diameter in the range from 1.5 mm to 3 mm, usually from 1.75 mm to 2 mm. The nature of the shearing body will be as generally described above in connection with the methods of the present invention.

In the exemplary embodiments, the catheter system will further comprise a drive motor assembly which may be coupled to a proximal portion of the inner catheter shaft to rotate the inner catheter shaft. Optionally, the drive motor assembly will also be attached to the sheath, where the sheath is held stationary while the inner catheter shaft is rotated. Preferably, the drive motor assembly permits the inner catheter shaft to be axially translated relative to the sheath so that the shearing body can be released from and drawn into the cavity while the inner catheter shaft and sheath remain coupled to the drive motor assembly.

Apparatus according to the present invention further comprise catheters including a catheter shaft having a proximal end and a distal end, and a shearing body disposed near the distal end of the catheter shaft. The shearing body is configured to engage an interface envelope defined by a stent embedded within stenotic material in a blood vessel when the shearing body is displaced therein. Suitable shearing bodies may have any of the configurations described above in connection with the method of the present invention. In an exemplary embodiment, the shearing body comprises a helical row of radially aligned filaments, typically having lengths in the range from 1.5 mm to 2 mm. In some cases, the helical row will be tapered with longer filaments (1.5 mm to 2 mm) at one end and progressively shorter filaments in the proximal or distal direction. Alternatively, the shearing body may comprise a brush having both radially short filament, e.g. having a length in the range from 0.25 mm to 0.5 mm, and radially long filaments, e.g. having lengths in the range from 1 mm to 2 mm.

In yet another specific aspect of the apparatus of the present invention, catheter kits comprise a catheter or catheter system and instructions for use of the catheter system. The catheter will include a catheter shaft having a proximal end and a distal end, and a shearing body disposed near the distal end of the catheter shaft. The instructions for use set forth that the shearing body is to be percutaneously introduced on one side of a restenosed stent within a blood vessel. The shearing body is then to be translated and rotated through the stent to dislodge stenotic material from an interface envelope defined by the stent. The kit will usually include sterile packaging, such as a pouch, box, enclosure, or the like, of a type normally employed for packaging and storing medical devices. The instructions for use will typically be included on a separate sheet of paper or booklet within the package and/or printed on a portion of the package itself.

BRIEF DESCRIPTION OF THE DRAWINGS

FIG. 1 is a perspective view of a blood vessel with portions broken away to show a stent embedded in a region of restenosis.

FIG. 2 is cross section view taken of along line 2—2 of FIG. 1.

FIG. 3 is a perspective view of a catheter system having a shearing body constructed in accordance with the principles of the present invention.

FIG. 4 is a detailed view of a portion of the catheter system of FIG. 3, shown in cross-section.

FIG. 5 is a detailed view of portion of the catheter system of FIG. 3, shown with the shearing body retracted within a sheath.

FIGS. 6A and 6B illustrate a shearing body, similar to that shown in FIG. 3, further comprising a distal filter element.

FIG. 7 is an enlarged view of a motor drive unit employed by the catheter system of FIG. 3.

FIG. 8 is a detailed view of a specific construction for a shearing body useful in the catheter system of FIG. 3.

FIG. 9 is an enlarged detailed view of a portion of a filament assembly useful for the construction of the shearing body of FIG. 8.

FIG. 10 is an alternative detailed view of a filament assembly useful for the construction of a shearing body in accordance with the principles of the present invention.

FIG. 11 illustrates an alternative shearing body construction employing both short and long filaments.

FIG. 12 illustrates another alternative shearing body construction using non-linear filaments.

FIG. 13 illustrates a shearing body comprising axially aligned elongate elements.

FIG. 14 a shearing body comprising counter-wound helical elements.

FIG. 15 illustrates a shearing body comprising a helically-wound continuous web of material.

FIG. 16 illustrates a shearing body comprising a plurality of axially spaced-apart disk elements.

FIG. 17 illustrates a shearing body comprising a perforate solid body.

FIGS. 18A–18E illustrate a method according to the present invention employing the catheter of FIG. 3.

FIG. 20 illustrates a kit including a catheter, a package, and instructions for use according to the present invention.

DESCRIPTION OF THE PREFERRED EMBODIMENT

Figure 19A:
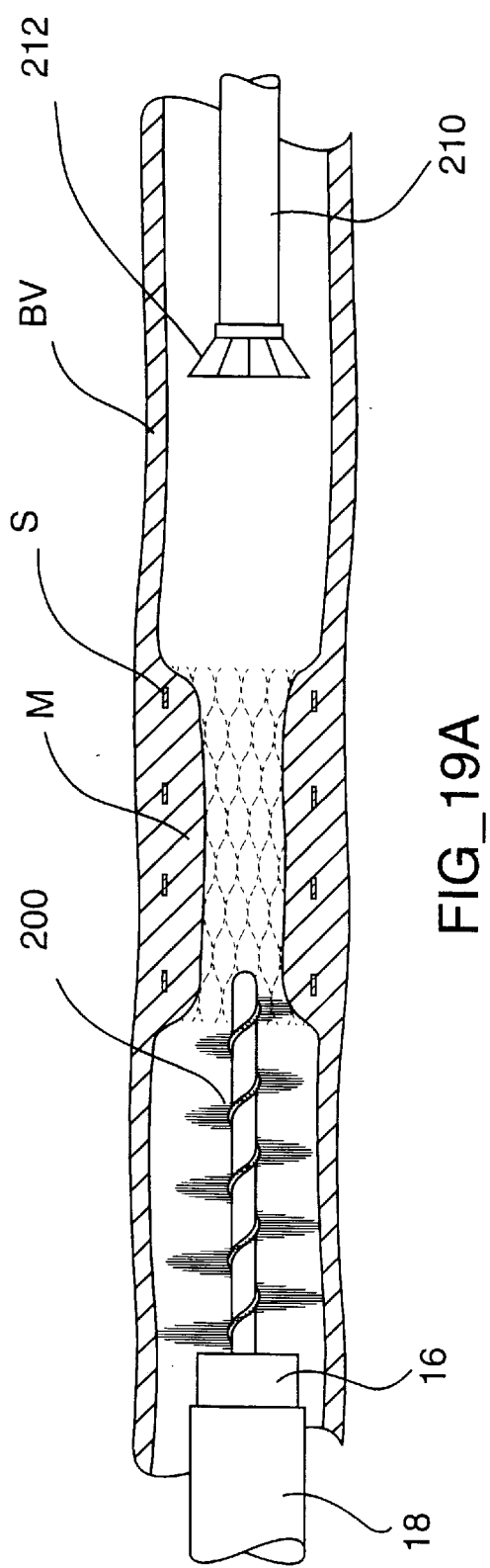
FIGS. 19A–19B illustrate an alternative method according to the present invention employing a brush-like shearing body and down-stream emboli collection.

The present invention provides apparatus and methods for treating restenosis which can occur in blood vessels following stent placement. Although stents are themselves intended to inhibit restenosis following a primary treatment, such as angioplasty or atherectomy, it has been found that in a significant number of cases, cell proliferation and/or thrombus formation occur to such an extent that blood flow through the stented lumen is significantly impaired. The result of such restenosis in a previously stented region of a blood vessel, such as a coronary or other artery, is schematically illustrated in FIGS. 1 and 2. As can be seen, a stent S can become embedded in a matrix M of stenotic material within an artery A. The resulting lumen L can thus become very restricted. While the stent S is illustrated as a Palmaz-Schatz stent of the type available from Johnson and Johnson Interventional Systems, it will be appreciated that such restenosis can occur in virtually any conventional stent having opening or interstices in the wall of the stent, including the Gianturco stent, available from Cook, Inc., the Walstent, available from Pfizer, Inc., and the like.

Of particular importance to the present invention, the stent S defines an interface envelope within the matrix M of stenotic material, as best observed in FIG. 2. The interface envelope will be generally cylindrical, but will usually display eccentricities resulting from the initial implantation in a non-cylindrical blood vessel lumen. As the stent will be formed from a material which is significantly harder than the stenotic material, usually being composed of stainless steel, tantalum, titanium, nitinol, or other metals, the interface envelope defines a barrier within the matrix M. The present invention relies on the interface envelope barrier to define the extent of the recanalization procedure which is performed. In particular, the present invention will provide for shearing and/or abrasion of substantially all of the stenotic material from within the interface envelope in a manner which is relatively non-traumatic to the patient and which does not significantly damage the stent itself.

The present invention relies on displacement of a shearing body within the interface envelope to dislodge the stenotic material from the interior of the stent S. While the shearing body may take a variety of specific forms, it will generally be a compliant structure having a width (diameter in the case of circular or cylindrical shearing bodies) which is slightly greater than the maximum diameter or width of the interior surface of the deployed stent. The size of the stent will be known from the patient records and/or can be determined by known diagnostic techniques, such as fluoroscopy, intravascular ultrasound (IVUS), or the like. The size of the shearing body can then be chosen to be slightly greater than the interior diameter or width of the stent, typically being at least 1% greater in width, preferably being from 1% to 25% greater, more preferably being from 2% to 20% greater, and still more preferably being from 5% to 15% greater in width.

The shearing body will comprise an exterior surface which, when displaced within the stented region of the blood vessel, will act to shear or abrade the stenotic material from the interface envelope defined by the stent. The shearing body may comprise a solid, expansible body, e.g. a sponge-like mass optionally embedded with abrasive particles or other elements over its exterior surface, but will more usually comprise a series of discontinuous elements, such as brush filaments, fabric disks, a helically wound row of fabric or other materials, expansible cages, and the like. Specific examples of each of these constructions will be described in greater detail below.

The shearing body will be displaced within the stented region of the blood vessel. Such displacement will comprise at least axial translation, i.e. motion along the axis of the blood vessel, or rotation, i.e. rotation about the axis of the blood vessel. More usually, the displacement will comprise simultaneous rotation and axial translation so that the surface of the shearing body is continuously swept about the inner periphery of the interface envelope as the shearing body is axially advanced through the matrix of stenotic material. It will be appreciated that displacement of the shearing body may also comprise axial and/or rotational oscillation. Frequently, such axial and rotational oscillation may be superimposed over the translation and rotation of the shearing body through the stenotic material.

The compliant nature of the shearing body may be achieved in a variety of ways. In the case of the brush-like shearing bodies, the individual filaments or other elements of the brush will themselves be flexible and capable of bending or folding in order to compress as the shearing body is introduced into the stented region of the blood vessel. Similarly, a fabric or membrane material used to form a helical row or axially spaced-apart disks will be sufficiently flexible so that it can be compressed to accommodate passage through the stented region of the blood vessel. Cage structures will usually be resilient and constructed so that they can spring open and closed so that they will radially compress as they enter the stented region. Sponges and other continuous body structures will be composed of or fabricated from materials which are inherently sufficiently compressible so that they may be compressed or constricted to accommodate the reduced diameter of the stented region. A variety of other structures will also be capable of providing this degree of compliance and compressibility. It will be appreciated, however, that all of these structures will also possess a sufficient resilience so that they will radially expand as the stenotic material is removed. It is desirable that the shearing body be able to assume a width or diameter which is sufficiently large so that it will engage the interior surface of the stent (i.e. the interface envelope defined by the stent) as the shearing body is displaced therein. In this way, the shearing body will be able to sweep the interior surface of the stent to recanalize the stented region within the blood vessel.

Optionally, the shearing body may have an adjustable width or diameter. That is, the catheter systems of the present invention may provide the user with the ability to selectively adjust a radial dimension of the shearing body, typically the diameter or width. As illustrated in more detail below, expansible cages may be provided where the axial dimension may be adjusted in order to expand or contract the radial dimension. The use of such radially adjustable shearing bodies may be advantageous since the shearing body may be introduced in a narrow width configuration and subsequently expanded as the shearing body is rotated or otherwise displaced in order to incrementally shear or abrade the stenotic material from the lumen within the stented region of the blood vessel. For example, the width of the shearing body can be gradually increased until contact with the stent is detected. Such detection may be achieved in a variety of ways, including expansion to a preselected diameter (based on a known or measured width of the stent), detection of resistance to further expansion, and/or detection of a change in electrical (e.g. resistance, inductance and/or capacitance) or other characteristics based on contact with the stent.

The shearing or abrasive action provided by the shearing body may be solely mechanical or may be augmented by the application of heat, ultrasonic energy, radiofrequency energy, or the like. For example, when the shearing body comprises a metallic cage, as described in greater detail below, it will be possible to apply monopolar or bipolar radiofrequency energy in order to effect cutting and/or cauterizing of the stenotic material which is being removed. Similarly, it would be possible to enhance the mechanical displacement of the shearing body by superimposing ultrasonic vibrational energy.

The shearing body will preferably comprise intersticies or internal voids which permit entrapment of the stenotic material as it is dislodged from the interior of the stented region of the blood vessel. The nature of the intersticies or voids may vary widely, and the extent of such variation will be apparent from examination of the particular shearing bodies illustrated below. For example, brush elements will include rather large void regions between individual filaments of the brush. Helically wound filaments and webs will include spaces between the adjacent turns of the helix. Similarly, multiple disk elements will include spaces between each successive disk. Cages and basket structures will include significant interior volume for collecting the dislodged stenotic material, and sponge-like structures will also include significant internal void volumes which can collect the stenotic material.

The present invention is not limited to shearing bodies having such intersticies or void volumes. For example, the inflatable balloons and other structures described previously may not have such void volumes (although balloons can be configured in helices and spirals which will have void volumes). Similarly, shearing bodies which comprise a single disk or other single, discrete elements may not have void volumes. In such cases, it will usually be desirable to provide an emboli collection ability apart from the shearing body itself.

The catheter systems of the present invention, regardless of the nature of the shearing body, will usually be provided with an ability to collect and remove emboli which are dislodged by the shearing body. In an illustrated embodiment below, the collection ability it provided by an aspiration catheter which is coaxially mounted over a catheter shaft which carries the shearing body. In an alternative embodiment below, the collection is provided by a separate emboli aspiration catheter which may be separately introduced to the patient, e.g. through a separate femoral access tract. A variety of other specific emboli collection devices and methods will be suitable for use with the present invention.

The shearing bodies described thus far are intended for percutaneous, intravascular introduction using a suitable catheter or catheter system. The shearing body will usually be carried at the distal end of an inner catheter shaft having a relatively low profile, typically with a diameter in the range from 0.2 mm to 1 mm. The inner catheter shaft will usually have an internal lumen suitable for receiving a guidewire, and will have sufficient column strength and torsional rigidity to permit both axial translation and rotation of the shearing body from the proximal end of the shaft. Thus, the inner catheter shaft should be suitable to act as a drive cable for the shearing body. The inner catheter shaft may be a multi-filar and/or counterwound coil, a braid- or coil-reinforced polymeric tube, e.g. composed of polyimide, polyamide (nylon), or may be a hypotube or other flexible metallic structure. In some cases, it may be desirable to combine two or more of such structures in a single drive cable. For example, the proximal end of a drive cable may be formed from a relatively less-flexible structure, such as a hypotube, while the distal end is formed from a more flexible structure such as a multi-filar and/or counterwound coil. Specific constructions for such drive cables are well known in the art. See, for example U.S. Pat. No. 5,108,411, the full disclosure of which is incorporated herein by reference. The length of the inner catheter shaft will be sufficient to permit introduction of the shearing body to a target location within the vasculature. For introduction to the coronary arteries from a femoral access tract in the patient's groin, a length in the range from 90 cm to 150 cm, will typically be sufficient.

Catheter systems according to the present invention may further comprise a sheath for covering the shearing body during introduction. In the case of radially compressible (self-expanding) shearing bodies, the sheath may also act as a radial constraint, where retraction of the sheath permits radial expansion of the shearing body. The sheath will usually comprise a thin-walled tubular component which is axially slidable relative to the inner catheter shaft to permit retraction and deployment of the shearing body and will define a cavity which receives the shearing body. As described in more detail below, both the sheath and the inner catheter shaft will often be connected at their proximal ends to a drive motor which anchors to the sheath and permits rotation and/or axial translation of the inner catheter shaft. The sheath will usually be composed of a polymeric material such as a polyethylene, polyethyleneterephthalate, polypropylene, polyurethane, polyimide, polyamide (nylon), polyvinylchloride, or copolymers and mixtures thereof, or the like, and may readily be fabricated by conventional extrusion techniques. The sheath will typically have a length which is somewhat less than that of the inner catheter shaft, typically being from 5 cm to 50 cm shorter.

In addition to the inner catheter shaft and sheath, catheter systems according to the present invention may also include an outer catheter tube which is coaxially received over the sheath. Thus, the outer catheter tube will have a lumen diameter which is slightly greater than the sheath. Typically the sheath will have an outer diameter in the range from 0.5 mm to 1.5 mm, and the outer catheter tube will have a lumen diameter in the range from 1.5 mm to 3 mm. In a preferred configuration of the present invention, the outer catheter tube will include a proximal hub having an aspiration port. The hub will permit hemostatic attachment to the exterior of the sheath, and an annular lumen between the interior of the outer catheter tube and exterior of the sheath will be created. Such annular lumen will be useful for aspiration of emboli and other debris created during the recanalization procedures of the present invention. In particular, a vacuum source can be connected to the aspiration port, permitting aspiration of the emboli through the annular lumen.

Apparatus according to the present invention will further comprise catheter kits. Such kits will include any of the catheters and catheter systems described above in combination with instructions for use (IFU) setting forth the methods of the present invention. The catheter and instructions for use will typically be packaged together in conventional sterile packaging, such as a pouch, tray, box, or the like. The instructions for use will most commonly be printed on a separate sheet or in a separate booklet, but in some cases may be incorporated into other components of the packaging.

Methods according to the present invention are intended to position the shearing body adjacent to or within a stented region of the patient's vasculature. The shearing body is then deployed and displaced, generally as described above, in order to dislodge stenotic material from within the stenosed region. The methods will preferably further comprise collection and removal of the dislodged stenotic material from the vasculature. The shearing body will be deployed in a radially collapsed or constrained configuration and/or will be expanded to a width or diameter which is slightly larger than the stent to be treated, and will thereafter be displaced within and through the stented region in order to dislodge the stenotic material. In a first illustrated embodiment, the catheter system is deployed on one side of the stented region and the shearing body distally advanced to the opposite side of the stented region while in a radially constrained configuration. The shearing body is then radially expanded and drawn back toward the catheter in order to dislodge the stenotic material. Aspiration is provided through the catheter in order to collect and remove emboli and other debris. This method relies on the use of a single catheter, thus reducing trauma to the patient.

In a second illustrated embodiment, the two catheters are separately introduced to opposite sides of the stented region. The first of these catheters is used to deploy and advance the shearing body through the stented region in order to dislodge material. The second catheter is used to collect and remove the emboli and other debris which has been dislodged by the shearing body. It will be appreciated, of course, that in some cases it may be desirable to aspirate the debris through both catheters. It may be further desirable to provide filters, balloons, and other barriers to help isolate the region being treated and prevent the release of emboli during the procedure.

Referring now to FIGS. 3–5, a first exemplary catheter system constructed in accordance with the principles of the present invention will be described. The catheter system 10 includes an inner catheter shaft 12, a tubular sheath 14 slidably received over the inner catheter shaft, and optionally an outer catheter tube 16 coaxially and slidably received over the tubular sheath. For some clinical applications, the catheter assembly comprising the inner catheter shaft 12, tubular sheath 14, and outer catheter tube 16 may be introduced through a guide catheter 18. The guide catheter 18 is useful for directing the catheter assembly to a particular target location within the patient's vasculature. For example, a coronary guide catheter having a curved distal end can be used for selecting a particular coronary ostium to introduce the catheter assembly to the right or left coronary artery. The guide catheter 18 may also provide support for pushing, rotating and maneuvering the catheter assembly. Use of the guide catheter 18, however, may not be necessary for all applications. Moreover, it will often be possible to use conventional coronary guide catheters in the methods and systems of the present invention.

Each of the inner catheter shaft 12, tubular sheath 14, outer catheter tube 16, and guide catheter 18 will have a distal end and a proximal end. Shearing body 20 is disposed at the distal end of the inner catheter shaft 12, and drive motor assembly 22 is attached to the proximal end of the inner catheter shaft 12. In general, the distal end of each of the catheter system components will be that which enters into the patient's vasculature while the proximal end is that which remains outside of the vasculature. Access to the vasculature will usually be through the femoral artery in the patient's groin or through the radial or brachial artery in the patient's arm using a conventional access sheath having a hemostasis valve (not illustrated). Intravascular access to the coronary arteries or other target locations will be provided over a conventional guidewire GW. The outer catheter tube 16 will include a hub 24 at its proximal end, and the hub includes both the hemostasis port 26 and an aspiration port 28. The guide catheter 18 will include a conventional hemostasis port 30 at its proximal end.

The shearing body 20 comprises a brush structure including a helical row of filaments 34 arranged in a spiral pattern. A small-diameter end of the spiral is positioned proximally and the large-diameter end of the spiral is positioned distally. The diameter of the small-diameter end is approximately equal to that of the inner catheter shaft 12, i.e. in the range from 0.2 mm to 1 mm, while the diameter of the large-diameter end is in the range from 3 mm to 5 mm, with the particular diameter chosen based on the diameter of the stent to be treated. The individual filaments may be composed of a polymeric material or metal, as described above. The filaments will usually have a diameter in the range from 0.05 mm to 0.15 mm, typically from 0.07 mm to 0.13 mm, with a length depending on their axial position within the shearing body 20. The total length of the shearing body in the axial direction will typically be in the range from 5 mm to 40 mm.

As best observed in FIGS. 4 and 5, the helical rows 34 of the shearing body are radially collapsed when drawn proximally into the sheath 14 (FIG. 5). When distally advanced, the rows 34 will radially expand due to their own resiliency. In a preferred construction, the filaments of helical rows 34 are attached at their radially inward ends to a spirally wound filament 36. The filament 36 is wound about the exterior of the inner catheter shaft 12, and will usually be an extension or part of a helical reinforcement coil 38 which extends proximally over a portion or all of the inner catheter shaft. An annular aspiration lumen 40 defined between the exterior surface of sheath 14 and the interior luminal surface of outer catheter tube 16 can be seen in FIG. 4.

A modification of the shearing body 20 is illustrated in FIGS. 6A and 6B. Shearing body 20A includes successive helical turns 34 of the tapered shearing body, identical to shearing body 20 as shown in FIG. 3. In addition, a filter assembly 50 is attached near the distal end of the inner catheter shaft 12. Filter assembly 50 comprises a series of four axially adjacent filter elements 52. The filter elements 52 may be composed of any of the materials listed above suitable for filaments 34. The filter elements 52, however, will generally have a greater density which will prevent passage of the emboli through the filter assembly 50.

FIG. 6B is an end view of a single filter element 52 of the filter assembly 50. Each filter element 52 comprises a multiplicity of fibers 53 which extend generally radially from the inner catheter shaft 12. In the illustrated embodiment, the individual fibers are shown to be kinked and arranged in a randomly overlapping pattern in order to define a filtering structure with a "pore size" sufficiently small to entrap larger emboli particles, typically those above 0.15 mm in size, yet sufficiently open to permit adequate blood flow during the procedure to avoid ischemia. The individual fibers 53, of course, could be arranged in other patterns, such as serpentine, helical, spiral, and the like in order to provide a desired density for the filter elements 52.

The filter assembly 50 is shown to be directly mounted on the inner catheter shaft 12 at a point distally of the shearing body 20A. Optionally, the filter assembly 50 may be mounted to freely rotate on the inner catheter shaft so that the filter assembly itself does not rotate during rotation of the shearing body 20A. Alternatively, the filter assembly 50 or an equivalent structure could be mounted on a separate filter support wire (not shown) which extends through the guidewire lumen of the inner catheter shaft 12.

In order to provide a filter element 52 having a relatively uniform porosity in the radial direction, the degree of kinking or bending of the individual fibers 53 can increase in the radially outward direction. In this way, the density provided by the randomly overlapping individual fibers 53 will remain generally uniform over the entire surface of the filter element 52. When multiple filter elements 52 are arranged in a space-part manner, as shown in FIG. 6A, the individual filter elements may have differing porosities in order to provide a porosity gradient in the axial direction. In this way, the filter assembly can more effectively capture small emboli without plugging because the large emboli will be captured by the upstream filter elements 52 with a larger pore size.

The filter assembly 50 will be sufficiently flexible so that it may be collapsed for both delivery from sheath 14 and the recapture within outer catheter tube 16. In addition to the filament assemblies described above, the filter assemblies could also be formed from woven, braided, or knit materials, or non-woven porous membranes and fabrics.

The drive motor assembly 22 is best illustrated in FIG. 7. Assembly 22 comprises a motor 60 having a spindle 62 which engages and drives a sleeve assembly 64. The inner catheter shaft 12 (not shown in FIG. 7) is received through a passage 66 in the distal end of the drive motor assembly 22 and captured in the sleeve assembly 64. The inner catheter shaft 12 will continue through the proximal portion of passage 66 and is rotatably received in an O-ring 61. A guidewire passing through the inner catheter shaft 12 may pass out through a hemostatic seal 63 at the proximal end of the passage 66. A port 65 is optionally provided on the drive motor assembly 22 proximally of the O-ring 61 in order to aspirate and/or perfuse fluids through the inner lumen of inner catheter shaft 12, particularly when the guidewire is withdrawn therefrom.

The sleeve assembly 64 comprises a compression fitting 67 which may be engaged against an exterior surface of inner catheter shaft 12 by tightening on knob 69 which is threadably attached to the portion of the assembly which engages spindle 62. In this way, the sleeve assembly can be tightened on to the inner catheter shaft 12 and thereafter driven by motor 60.

The inner catheter shaft 12 will be axially advanced and retracted relative to the outer catheter tube 16 by moving the drive motor assembly 22 relative to the proximal hub 24 of the outer catheter tube. Usually, this will be done manually. Optionally, mechanical assemblies may be provided in order to anchor the proximal end of the outer catheter tube 16 and translate the drive motor relative to the hub and in order to advance and retract the shearing body 20.

Usually, the sheath 14 will be removed prior to rotating the inner catheter shaft 12 with the drive motor assembly 20. For example, the sheath 14 may be a splittable sheath which can be pulled apart and axially split as it is withdrawn from outer catheter tube 16. Alternatively, as illustrated in FIG. 3, the sheath 14 may be proximally retracted into a cavity 80 formed coaxially with the passage 66. In this way, the sheath will be held stationary (immobilized) as the inner catheter shaft 12 is rotated by the drive motor assembly 22. As a further alternative, the sheath 14 may be removed prior to attaching the drive motor assembly. As a still further alternative, the sheath 14 could be removed together with the guidewire through the hemostasis seal 63. Generally, however, removing the sheath 14 entirely will be preferred since it will increase the available area of the annular aspiration lumen defined between the exterior of the inner catheter shaft 12 and the interior of the outer catheter tube 16.

Referring now to FIGS. 8 and 9, a particular method for fabricating a shearing body according to the present invention will be described. The inner catheter shaft 12 is wrapped with a spiral filament 36 generally as described above. Radial filaments 90 are provided in the form of U-shaped elements which may be placed over the filament 36 as best seen in FIG. 9. The filament 36 is then wound around the shaft 12 to provide a helical row of filaments. The spiral filament 36 extends proximally down the shaft 12 with successive turns becoming progressively closer. Eventually, the coil 36 is intertwined with turns of a separate helical reinforcement coil 92 which extends proximally down the shaft 12 to form a multi-filar drive cable.

A second alternative for forming brush filaments suitable for helically wrapping around the inner catheter shaft 12 is illustrated in FIG. 10. There, a flat sheet of material may be machined, photochemically etched, or otherwise patterned to have an array of comb-like elements 96 extending from a base 98. The base 98 may then be wrapped around and attached to the inner catheter shaft 12.

Referring now to FIG. 11, an alternative embodiment of a shearing body 100 which may be attached to the distal end of inner catheter shaft 12 as illustrated. The shearing body 100 includes a plurality of both short elements 102 and long elements 104. The shorter elements typically have a length in the range from 0.25 mm to 0.5 mm and the long filaments have a length in the range from 1 mm to 2 mm. Preferably, the long elements 104 will all be curved or deflected near their radially outward ends to present axially aligned region for sweeping against the interface envelope as the shearing body 100 is rotated within the stented region of a blood vessel (optionally having a hook-like configuration to help entrap the dislodged stenotic material). The filaments 102 and 104 may be composed of the same or different materials, including any of the materials described above for use in the previous embodiments. The shearing body 100 is shown with a generally cylindrical (uniform diameter) configuration, but could readily be adapted to have a tapered configuration as previously described.

FIG. 12, is an end view of another shearing body 110 comprising generally radially aligned brush filaments. The brush filaments 112 are shown to be kinked, similar to the configuration of the filter elements 52 in FIG. 6B, resulting in a highly irregular network which is particularly efficient for entrapping thrombus dislodged by the shearing body 10. It will be appreciated that the kinked filaments of 112 could be combined with any of the other filaments of the other embodiments to provide brush structures having different regions with different removal and entrapment characteristics.

A variety of other shearing body configurations are illustrated in FIGS. 13–17. In FIG. 13, a cage-type shearing body 120 is mounted at the distal end of inner catheter shaft 12. The cage 120 comprises a plurality of axially aligned resilient elements 122, and each of the individual elements is shaped so that the shearing body 120 has a generally cylindrical, large-diameter configuration when unconstrained. The elements 122 can be round filaments, ribbon filaments, or have a variety of other cross-sections, and be formed from virtually any of the polymeric materials and metals described above for use as brush filaments. The elements are attached to the inner catheter shaft 12 by a distal ring 124 and a proximal ring 126. Usually, the distal ring 124 will be fixed to the shaft 12, while the proximal ring 126 will be free to axially translate over the shaft as the elements 122 are radially collapsed or expanded. It will be appreciated, of course, that a rod or shaft (not shown) could be attached to ring 26 so that the elements 122 could be selectively expanded or contracted by axial motion of the rod or shaft. In this way, the diameter of shearing body 120 could be selectively adjusted from the proximal end of the shaft.

Shearing body 130 illustrated in FIG. 14 is similar to the cage structure of shearing body 20. Instead of axial elements 122, however, shearing body 130 comprises counter-wound helical elements 132 and 134. The helical elements 132 and 134 may comprise round filaments, ribbon filaments, or the like, and may be composed of virtually any of the polymeric materials and metals described above for use as brush filaments. The helical elements are attached in a distal ring 136 and proximal 138. The proximal ring 138 may be free to slide over the shaft 12 and may be optionally be attached to a rod, sleeve, or other means for axially translating the ring in order to adjust the radius of the shearing body 130.

FIG. 15 illustrates a shearing body 140 comprising a continuous web of material arranged in a helical pattern. The material may be a fabric, membrane, or other continuous structure of a compliant or flexible nature. For example, the continuous web of material may be formed from polyamides (nylon), polyimides, polyethylenes, polyethyleneterephthalates, polypropylenes, latex rubbers, silicone rubbers, and mixtures and combinations thereof. The continuous web 142 will be helically wrapped in a manner analogous to the brush filaments described previously. As shown, the helical web is in a cylindrical arrangement. The web, of course, could be arranged in a tapered pattern as previously discussed.

Shearing body 150 in FIG. 16 comprises a plurality of axially-spaced apart disks 152. The disks are composed of a fabric or membrane, preferably polyamides (nylon), polyimides, polyethylenes, polyethyleneterephthalates, polypropylenes, latex rubbers, silicone rubbers, and mixtures and combinations thereof. The disks define interstices therebetween for entrapping stenotic material which has been dislodged from within the stent. Disks are shown in a cylindrical arrangement, but could readily be adapted to a tapered configuration.

Shearing body 160 illustrated in FIG. 16 comprises a solid expansible body, typically in a sponge-like configuration, such as open cell plastic foams, reticulated fibrous networks, natural sponge material, and the like. The plastic foams are preferably formed from polyurethane or polyethylene, while the reticulated fibrous networks may be formed from any of the polymeric fiber materials listed above for use as brush filaments. Abrasive particles or other elements may be incorporated in the exterior surface of the body 162, and voids 164 within the body are suitable for entrapping stenotic materials which has been dislodged from within the stented region.

Referring now to FIGS. 18A–18E use of the catheter system 10 for removing stenotic material M from within a stent S and a blood vessel BV will be described. The catheter system is introduced in a conventional percutaneous intravascular manner so that the distal end of outer catheter tube 16 is positioned adjacent to one side of the restenosed area having stent S therein, as illustrated in FIG. 18A. Generally, the catheter system 10 will be operated with the guidewire GW in place in order to permit catheter exchange and/or advance of the catheter system or components thereof for treating other lesions. If desired, however, the guidewire GW may be removed after a lesion has been crossed with the shearing body. Sheath 14 is then distally extended over guidewire GW until its distal end lies beyond the stented region, as shown in FIG. 18B. The sheath 14 is then withdrawn (and optionally removed from the catheter system 10) and/or the inner catheter tube 12 extended so that the shearing body 20 lies beyond the stented region, as illustrated in FIG. 18C. The shearing body is then rotated, typically at a rotational speed in the range from 10 rpm to 10,000 rpm, usually from 60 rpm to 6000 rpm, and axially drawn in the proximal direction so that it passes through the stenotic material M, as illustrated in FIG. 18D. The stenotic material is sheared from within the interface envelope by stent S with the resulting particulate material being captured within adjacent turns of the filaments of the shearing body 20, also as illustrated in FIG. 18D. Aspiration is applied through the port 28 so that some of the particles are drawn into the distal end of outer catheter tube 16. The shearing body continues to be drawn in the proximal direction, with aspiration applied, until the shearing body is recaptured within the sheath 16, leaving the stented region recanalized and substantially free from stenotic material with the stent S as shown in FIG. 18E. By rotating the helical shearing body 20 in the direction shown by the arrow in FIG. 18D, the helical row acts to "pump" stenotic material and other debris toward the distal end of the outer catheter tube 16. By combining such pumping action with aspiration within the outer catheter tube 16, efficient collection of the stenotic material and other debris can be accomplished. Such pumping can be provided by any of the helical shearing body arrangements described herein.

Figure 19B:
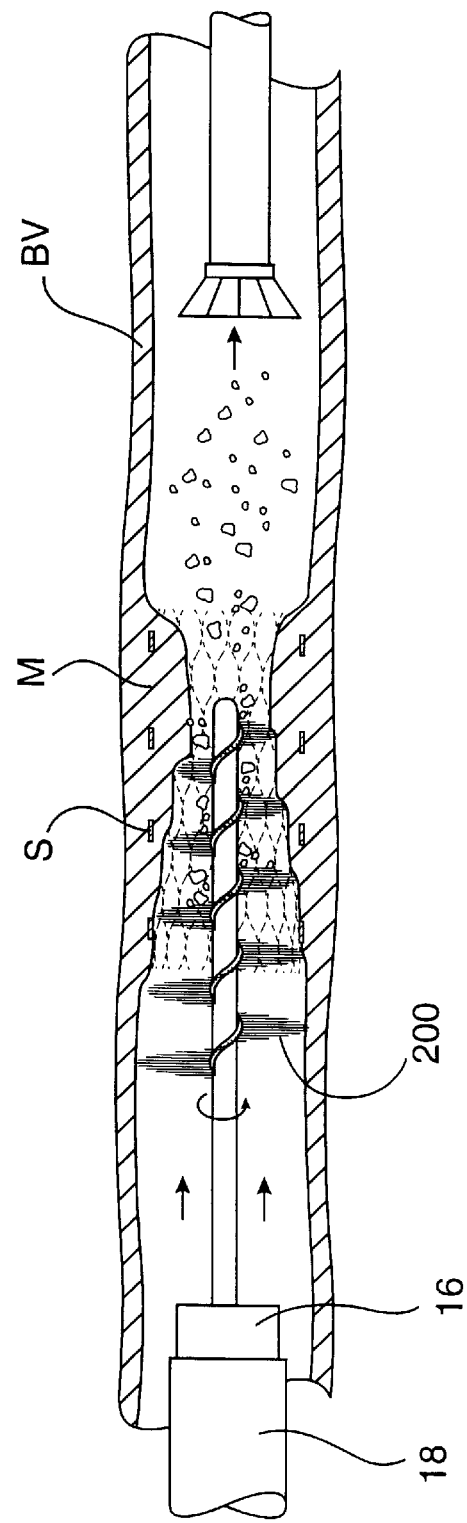

An alternative method for removing stenotic material M from within a stent S in a blood vessel BV is shown in FIGS. 19A and 19B. The catheter sheath 16 is deployed adjacent one side of the stenotic material M, as shown in FIG. 19A, and a brush-like shearing body 200 is advanced distally from the distal end thereof. Brush 200 is rotated and axially advanced (in the distal direction) through the stenotic material M. A second catheter 210 is positioned on the opposite side of stenotic material M and comprises an expandable skirt 212 which assists in capturing emboli released during the recanalization process. The skirt 212 may conveniently comprise a perforate structure, such as a wire mesh, so that blood flow can be maintained during the procedure. Aspiration will be provided through the catheter 210 to enhance collection of emboli. Shown in FIG. 19B, the brush 200 continues to be rotated and distally advanced through the stenotic material M, until the region is fully recanalized.

Referring now to FIG. 20, a catheter kit according to present invention comprises a catheter or catheter system 300, often mounted on a board 302, instructions for use (IFU), and a pouch or other conventional package 304. The instructions for use IFU are typically part of a separate sheet or booklet which, together with the catheter 300, is packaged within the pouch or other packaging material 304. The packaging will preferably be sterile or sterilizable. The instructions for use IFU will set forth methods steps comprising the method(s) as described above.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter system comprising:
   an inner catheter shaft having a proximal end and a distal end;
   a radially compressible compliant shearing body disposed near the distal end of the inner catheter shaft, wherein the shearing body has a first end and a second end and wherein the shearing body is tapered so that one end is larger than the other; and
   a sheath having a proximal end, a distal end, and a cavity near the distal end, wherein the inner catheter is slidably coupled to the sheath so that the compliant shearing body can be radially constrained within and released from the cavity.

2. A catheter system as in claim 1, further comprising an outer catheter tube having a proximal end, a distal end, and a lumen therethrough, wherein the outer catheter tube comprises a hub at its proximal end, said hub having an aspiration port.

3. A catheter system as in claim 1, wherein the inner catheter shaft has a guidewire lumen extending from the proximal end to the distal end.

4. A catheter system as in claim 2, wherein the inner catheter shaft has a diameter in the range from 0.2 mm to 1 mm, the shearing body has a maximum width when radially unconstrained in the range of 2 mm to 5 mm, the sheath cavity has a diameter in the range from 0.75 mm to 2 mm, and the outer catheter tube has a lumen diameter in the range from 1.5 mm to 3 mm.

5. A catheter system as in claim 1, wherein at least a portion of the shearing body has a generally round cross-section.

6. A catheter system as in claim 1, wherein at least a portion of the shearing body has a polygonal cross-section.

7. A catheter system as in claim 1, wherein the shearing body comprises an axially elongate surface.

8. A catheter system as in claim 1, wherein the shearing body comprises a helical row.

9. A catheter system as in claim 8, wherein the helical row comprises a helically aligned radially oriented filaments.

10. A catheter system as in claim 8, wherein the helical row comprises a continuous web of material.

11. A catheter system as in claim 1, wherein the shearing body comprises a brush.

12. A catheter system as in claim 1, wherein the shearing body comprises a cage.

13. A catheter system as in claim 1, wherein the shearing body is compliant with an unconstrained width greater than the width of the sheath cavity so that the shearing body may be radially constrained within said cavity.

14. A catheter system as in claim 1, wherein the shearing body may be expanded by application of a compressive force in the axial direction, further comprising means for applying an axially compressive force to the shearing body.

15. A catheter system as in claim 1, further comprising a drive motor assembly which may be coupled to a proximal portion of the inner catheter shaft to rotate the inner catheter shaft.

16. A catheter system as in claim 15, wherein the drive motor assembly may also be attached to a proximal portion of the sheath, wherein the sheath is held stationary while the inner catheter shaft is rotated therein.

17. A catheter system as in claim 16, wherein the drive motor assembly permits the inner catheter shaft to be axially translated relative to the sheath so that the compliant shearing body can be released from and drawn into the cavity while the inner catheter shaft and sheath remain coupled to the drive motor assembly.

18. A catheter system comprising:

an inner catheter shaft having a proximal end and a distal end;

a radially compressible helical row of radially oriented filaments disposed near the distal end of the inner catheter shaft; and a sheath having a proximal end, a distal end, and a cavity near the distal end, wherein the inner catheter is slidably coupled to the sheath so that the compliant shearing body can be radially constrained within and released from the cavity.

19. A catheter system as in claim 18, further comprising an outer catheter tube having a proximal end, a distal end, and a lumen therethrough, wherein the outer catheter tube comprises a hub at its proximal end, said hub having an aspiration port.

20. A catheter system as in claim 18, wherein the inner catheter shaft has a guidewire lumen extending from the proximal end to the distal end.

21. A catheter system as in claim 20, wherein the inner catheter shaft has a diameter in the range from 0.2 mm to 1 mm, the helical row has a maximum width when radially unconstrained in the range of 2 mm to 5 mm, the sheath cavity has a diameter in the range from 0.75 mm to 2 mm, and the outer catheter tube has a lumen diameter in the range from 1.5 mm to 3 mm.

22. A catheter system as in claim 18, wherein at least a portion of the helical row has a generally round cross-section.

23. A catheter system as in claim 18, wherein at least a portion of the helical row has a polygonal cross-section.

24. A catheter system as in claim 18, wherein the helical row is tapered at at least one end, with said one end having a smaller width than other portions of the helical row.

25. A catheter system as in claim 18, wherein the helical row is compliant with an unconstrained width greater than the width of the sheath cavity so that the shearing body may be radially constrained within said cavity.

26. A catheter system as in claim 18, further comprising a drive motor assembly which may be coupled to a proximal portion of the inner catheter shaft to rotate the inner catheter shaft.

27. A catheter system as in claim 26, wherein the drive motor assembly may also be attached to a proximal portion of the sheath, wherein the sheath is held stationary while the inner catheter shaft is rotated therein.

28. A catheter system as in claim 27, wherein the drive motor assembly permits the inner catheter shaft to be axially translated relative to the sheath so that the compliant shearing body can be released from and drawn into the cavity while the inner catheter shaft and sheath remain coupled to the drive motor assembly.

* * * * *